（12） United States Patent
Hassan et al.

(10) Patent No.: US 9,067,859 B2
(45) Date of Patent: Jun. 30, 2015

(54) HIGH SHEAR ROTARY FIXED BED REACTOR

(75) Inventors: Abbas Hassan, Sugar Land, TX (US); Rayford G. Anthony, College Station, TX (US); Gregory Borsinger, Chatham, NJ (US); Aziz Hassan, Sugar Land, TX (US); Ebrahim Bagherzadeh, Sugar Land, TX (US)

(73) Assignee: H R D CORPORATION, Houston, TX (US)

( * ) Notice: Subject to any disclaimer, the term of this patent is extended or adjusted under 35 U.S.C. 154(b) by 974 days.

(21) Appl. No.: 12/476,415

(22) Filed: Jun. 2, 2009

(65) Prior Publication Data

US 2010/0004419 A1 Jan. 7, 2010

Related U.S. Application Data

(60) Provisional application No. 61/078,132, filed on Jul. 3, 2008.

(51) Int. Cl.
    *C07C 51/36* (2006.01)
    *C07C 29/10* (2006.01)
    (Continued)

(52) U.S. Cl.
    CPC ........... *C07C 29/106* (2013.01); *B01F 7/00766* (2013.01); *B01F 7/00791* (2013.01);
    (Continued)

(58) Field of Classification Search
    CPC .......... F04B 53/00; C07C 53/00; B01J 19/18; C08F 110/06
    See application file for complete search history.

(56) References Cited

U.S. PATENT DOCUMENTS 3,767,535 A   10/1973   Havewala et al.
3,887,167 A   6/1975    Irwin
(Continued)

FOREIGN PATENT DOCUMENTS

GB   2276832     10/1994
GB   2276832 A   10/1994
(Continued)

OTHER PUBLICATIONS

International Search Report and Written Opinion dated Feb. 16, 2010 issued in corresponding Application No. PCT/US2009/045967, 10 pages.
(Continued)

*Primary Examiner* — In Suk Bullock
*Assistant Examiner* — Sharon Pregler
(74) *Attorney, Agent, or Firm* — Timothy S. Westby; Porter Hedges, LLP.

(57) ABSTRACT

A reactor comprising at least one contact surface made from, coated with, or impregnated by a catalyst, wherein the contact surface comprises a sintered metal or a ceramic, and wherein the reactor is configured to subject a reactant stream to shear. A system for carrying out a heterogeneously catalyzed reaction, the system comprising a reactor as described above and a pump configured for delivering reactants to the at least one reactor. A method for carrying out a heterogeneously-catalyzed reaction by introducing reactants into a reactor comprising at least one contact surface made from, coated with, or impregnated by a catalyst under conditions which promote production of a desired product, wherein the contact surface comprises a sintered metal or a ceramic, and forming a dispersion of reactants within the reactor, wherein the dispersion comprises droplets or gas bubbles of reactant with an average diameter of less than about 5 μm.

20 Claims, 2 Drawing Sheets

(51) Int. Cl.

| | |
|---|---|
| *B01F 7/00* | (2006.01) |
| *B01F 13/10* | (2006.01) |
| *B01J 8/20* | (2006.01) |
| *B01J 8/22* | (2006.01) |
| *B01J 10/00* | (2006.01) |
| *B01J 14/00* | (2006.01) |
| *B01J 19/00* | (2006.01) |
| *B01J 19/18* | (2006.01) |
| *C07C 29/04* | (2006.01) |
| *C07C 45/34* | (2006.01) |
| *C07C 45/39* | (2006.01) |
| *C07C 51/265* | (2006.01) |
| *C07C 67/08* | (2006.01) |
| *C07C 209/36* | (2006.01) |
| *C12C 11/02* | (2006.01) |

(52) U.S. Cl.
CPC ......... *B01F13/1013* (2013.01); *B01F 13/1016* (2013.01); *B01J 8/20* (2013.01); *B01J 8/22* (2013.01); *B01J 10/007* (2013.01); *B01J 14/005* (2013.01); *B01J 19/008* (2013.01); *B01J 19/1806* (2013.01); *B01J 2219/00105* (2013.01); *C07C 29/04* (2013.01); *C07C 45/34* (2013.01); *C07C 45/39* (2013.01); *C07C 51/265* (2013.01); *C07C 67/08* (2013.01); *C07C 209/36* (2013.01); *C07C 2101/16* (2013.01); *C12C 11/02* (2013.01)

(56) References Cited

U.S. PATENT DOCUMENTS

| | | | | |
|---|---|---|---|---|
| 3,996,012 | A | | 12/1976 | Zucker |
| 4,277,632 | A | | 7/1981 | Kumazawa |
| 5,167,782 | A | | 12/1992 | Marlow |
| 5,538,191 | A | * | 7/1996 | Holl .................................. 241/1 |
| 5,877,350 | A | | 3/1999 | Langer et al. |
| 6,368,366 | B1 | | 4/2002 | Langer et al. |
| 6,368,367 | B1 | | 4/2002 | Langer et al. |
| 6,383,237 | B1 | | 5/2002 | Langer et al. |
| 6,530,964 | B2 | | 3/2003 | Langer et al. |
| 6,742,774 | B2 | | 6/2004 | Holl |
| 2002/0089074 | A1 | * | 7/2002 | Holl ................................ 261/92 |
| 2003/0043690 | A1 | | 3/2003 | Holl |
| 2004/0052158 | A1 | | 3/2004 | Holl |
| 2004/0219079 | A1 | * | 11/2004 | Hagen et al. ................... 422/194 |
| 2005/0033069 | A1 | * | 2/2005 | Holl et al. ...................... 554/141 |
| 2005/0287025 | A1 | | 12/2005 | Eriksson et al. |
| 2006/0245991 | A1 | | 11/2006 | Holl |

FOREIGN PATENT DOCUMENTS

| | | |
|---|---|---|
| WO | 02064708 A2 | 8/2002 |
| WO | 2008122026 A1 | 10/2008 |

OTHER PUBLICATIONS

Guang-Wen Chu et al.; Micromixing Efficiency of a Novel Rotor-Stator Reactor; Chemical Engineering Journal, vol. 128, Apr. 2007, pp. 191-196.
"Caviation: A technology on the horizon," Current Science 91 (No. 1): 35-46 (2006).
Extended European Search Report dated Dec. 22, 2011 for corresponding European Patent Application No. 09773986.6.
IKA-Rotor-Stator Generators—2003 Processing Catalog (38 pgs.).
International Search Report and Written Opinion dated Feb. 16, 2010 issued for corresponding PCT Application No. PCT/US2009/045967 (10 pgs.).
Chinese Office Action dated Feb. 20, 2013 for corresponding Chinese Application No. 200980116881.3 (7 pgs.).
Office Action dated Jun. 3, 2011 for U.S. Appl. No. 12/568,280 (16 pgs.).
Office Action dated Jun. 2, 2011 for U.S. Appl. No. 12/427,286 (12 pgs.).
Office Action dated Jun. 25, 2009 for U.S. Appl. No. 12/142,447 (10 pgs.).
Office Action dated Jan. 7, 2010 for U.S. Appl. No. 12/142,447 (6 pgs.).
Office Action dated May 13, 2010 for U.S. Appl. No. 12/142,447 (5 pgs.).
Office Action dated Feb. 4, 2010 for U.S. Appl. No. 12/492,721 (5 pgs.).
Office Action dated Feb. 18, 2010 for U.S. Appl. No. 12/635,433 (6 pgs.).
Office Action dated Feb. 18, 2010 for U.S. Appl. No. 12/635,454 (6 pgs.).
Office Action dated May 14, 2010 for U.S. Appl. No. 12/137,441 (15 pgs.).
Office Action dated Feb. 19, 2010 for U.S. Appl. No. 12/144,459 (10 pgs.).
Office Action dated Sep. 2, 2009 for U.S. Appl. No. 12/142,433 (11 pgs.).
Office Action dated Jan. 29, 2010 for U.S. Appl. No. 12/142,433 (8 pgs.).
Office Action dated May 24, 2011 for U.S. Appl. No. 12/142,433 (10 pgs.).
Office Action dated Apr. 30, 2010 for U.S. Appl. No. 12/141,191 (12 pgs.).
Office Action dated Oct. 27, 2009 for U.S. Appl. No. 12/142,120 (15 pgs.).
Office Action dated May 5, 2010 for U.S. Appl. No. 12/571,537 (12 pgs.).
Office Action dated Feb. 24, 2011 for U.S. Appl. No. 12/796,358 (13 pgs.).
Office Action dated Feb. 29, 2012 for U.S. Appl. No. 12/146,733 (8 pgs.).
Office Action dated Jun. 3, 2011 for U.S. Appl. No. 12/568,155 (11 pgs.).
European Examination Report dated Jan. 31, 2013 for corresponding European Application No. 09773986.6 (4 pgs.).
Eurasian Office Action dated Feb. 14, 2013 for corresponding Eurasian Application No. 201100147 (2 pgs.).
Gulf Cooperation Council Examination Report dated May 13, 2013 for corresponding GCC Application No. GCC/P/2009/13801 (5 pgs.).
Eurasian Office Action dated Apr. 20, 2013 for corresponding Eurasian Application No. 201100147/31 (2 pgs.).
Chattopadhyay et al., "Understanding Mechanical Energy Driven Nonequilibrium Processing: Some Results, Eleventh International Conference on Rapidly Quenched and Metastable Materials," A Material Science and Engineering, vol. 375-377, dated Jul. 15, 2004, pp. 72-77 (9 pgs.).
India Examination Report dated Feb. 17, 2015 for corresponding India Application No. 6734/DELNP/2010 (2 pgs.).
Chinese Office Action dated Nov. 1, 2013 for corresponding Chinese Application No. 200980116981.3 (4 pgs.).

* cited by examiner

HIGH SHEAR ROTARY FIXED BED REACTOR

CROSS-REFERENCE TO RELATED APPLICATIONS

This application claims the benefit under 35 U.S.C. §119 (e) of U.S. Provisional Patent Application No. 61/078,132, filed Jul. 3, 2008, the disclosure of which is hereby incorporated herein by reference.

STATEMENT REGARDING FEDERALLY SPONSORED RESEARCH OR DEVELOPMENT

Not Applicable.

BACKGROUND

1. Technical Field

The present invention relates generally to heterogeneously catalyzed reactions. More particularly, the present invention relates to an apparatus and process for contacting reactants with a catalyst whereby a desired product is obtained.

2. Background of the Invention

The rate of chemical reactions involving liquids, gases and solids depend on time of contact, temperature, and pressure. In cases where it is desirable to react two or more raw materials of different phases (e.g. solid and liquid; liquid and gas; solid, liquid and gas), one of the limiting factors controlling the rate of reaction involves the contact time of the reactants. When reaction rates are accelerated, residence times may be decreased, thereby increasing obtainable throughput.

In the case of heterogeneously catalyzed reactions there is the additional rate limiting factor of having the reacted products removed from the surface of the solid catalyst to permit the catalyst to catalyze further reactants. Contact time for the reactants and/or catalyst is often controlled by mixing which provides contact with reactants involved in a chemical reaction.

Not to be limited by theory, it is known in emulsion chemistry that sub-micron particles, or bubbles, dispersed in a liquid undergo movement primarily through Brownian motion effects. Such sub-micron sized particles or bubbles may have greater mobility through boundary layers of solid catalyst particles, thereby facilitating and accelerating the catalytic reaction through enhanced transport of reactants.

The use of small sized solid catalyst particles in slurry reactors and fixed bed reactors presents problems. For example, in instances where the reaction to be catalyzed is highly exothermic (e.g., Fischer-Tropsch conversion of gases to liquid hydrocarbons), fixed bed operation may be unsuitable due to the inability to adequately control the reactor temperature. Slurry operation may overcome the temperature control issue, but concomitantly presents the issue of separating the small catalyst particles from the product prior to recycle, disposal and/or regeneration of the catalyst and sale or further processing of the product.

Accordingly, there is a need in industry for improved apparatus, systems and processes for contacting reactants with solid catalyst.

SUMMARY

Herein disclosed is a reactor comprising at least one contact surface made from, coated with, or impregnated by a catalyst, wherein the contact surface comprises a sintered metal or a ceramic. The reactor can comprise at least one rotor and at least one stator. The contact surface can comprise at least a portion of the at least one rotor, at least a portion of the at least one stator, or at least a portion of both the at least one rotor and the at least one stator. In embodiments, the at least one rotor is rotatable at a tip speed of at least 22.9 m/s (4,500 ft/min), wherein the tip speed is defined as $\pi Dn$, where D is the diameter of the rotor and n is the frequency of revolution. In embodiments, the at least one rotor is rotatable at a tip speed of at least 40.1 m/s (7,900 ft/min). In embodiments, the at least one rotor is rotatable at a tip speed of at least 225 m/s (44,200 ft/min). In embodiments, the at least one rotor is separated from the at least one stator by a shear gap in the range of from 1 μm (0.00004 inch) to about 4 mm (0.016 inch), wherein the shear gap is the minimum distance between the rotor and the stator. In embodiments, the shear rate provided by rotation of the at least one rotor during operation is at least 20,000 $s^{-1}$, wherein the shear rate is defined as the tip speed divided by the shear gap, and wherein the tip speed is defined as $\pi Dn$, where D is the diameter of the rotor and n is the frequency of revolution.

In embodiments, the reactor comprises at least two contact surfaces made from, coated with, or impregnated by catalyst. At least one contact surface may be made from, coated with, or impregnated by a different catalyst than at least one other contact surface. The reactor can comprise at least one rotor and at least one stator, wherein the at least one rotor comprises at least one ring of rotor tips, the at least one stator comprises at least one ring of stator tips, wherein the rotor tips and the stator tips are complementarily-shaped, and wherein the at least one contact surface comprises at least a portion of the at least one ring of the rotor, at least a portion of the at least one ring of the stator, or both. In embodiments, at least a portion of the at least one stator ring is made from, coated with, or impregnated by a catalyst and at least a portion of the at least one rotor ring is made from, coated with, or impregnated by a different catalyst. In embodiments, the reactor comprises at least two sets of complementarily-shaped rotor/stator rings, and a contact surface of one set of rings is made from, coated with, or impregnated by a different catalyst than a contact surface of another set of rotor/stator rings. In certain applications, the reactor comprises at least two generators, wherein each generator comprises a rotor and a complementarily-shaped stator. A contact surface of a first generator can be made from, coated with, or impregnated by a different catalyst than a contact surface of a second generator. A shear rate provided by one generator can be greater than, less than, or the same as a shear rate provided by another generator. In embodiments, the catalyst is selected from hydrogenation catalysts, hydroxylation catalysts, partial oxidation catalysts, hydrodesulfurization catalysts, hydrodenitrogenation catalysts, hydrofinishing catalysts, reforming catalysts, hydration catalysts, hydrocracking catalysts, Fischer-Tropsch catalysts, dehydrogenation catalysts, and polymerization catalysts.

Also disclosed herein is a system for carrying out a heterogeneously catalyzed reaction, the system comprising at least one reactor comprising at least one contact surface made from, coated with, or impregnated by a catalyst, wherein the contact surface comprises a sintered metal or a ceramic; and a pump configured for delivering reactants to the at least one reactor. In embodiments, the system comprises at least two reactors comprising at least one contact surface made from, coated with, or impregnated by a catalyst, wherein the contact surface comprises a sintered metal or a ceramic.

Also disclosed herein is a method for carrying out a heterogeneously-catalyzed reaction by introducing reactants into a reactor, the reactor comprising at least one contact surface made from, coated with, or impregnated by a catalyst under conditions which promote production of a desired product, wherein the contact surface comprises a sintered metal or a ceramic and forming a dispersion of the reactants within the reactor, wherein the dispersion comprises droplets or gas bubbles of reactant. The droplets or gas bubbles of reactant in the dispersion can have an average diameter of less than or equal to about 5 μm.

The reactor can comprise at least two contact surfaces made from, coated with, or impregnated by catalyst. At least one contact surface can be made from, coated with, or impregnated by a different catalyst than at least one other contact surface. In embodiments, the reactor comprises at least two generators, wherein each generator comprises a rotor and a complementarily-shaped stator, and wherein a contact surface of a first generator is made from, coated with, or impregnated by a different catalyst than a contact surface of a second generator. The catalyst can be chosen from hydrogenation catalysts, hydroxylation catalysts, partial oxidation catalysts, hydrodesulfurization catalysts, hydrodenitrogenation catalysts, hydrofinishing catalysts, reforming catalysts, hydration catalysts, hydrocracking catalysts, Fischer-Tropsch catalysts, dehydrogenation catalysts, polymerization catalysts, or combinations thereof. The reactor can further comprise at least one rotor and at least one stator separated by a shear gap, which is the minimum distance between the at least one rotor and the at least one stator, and the method can further comprise subjecting the reactants to a shear rate of at least 20,000 $s^{-1}$, wherein the shear rate is defined as the tip speed divided by the shear gap, and wherein the tip speed is defined as πDn, where D is the diameter of the at least one rotor and n is the frequency of revolution. In embodiments, subjecting the reactants to a shear rate of at least 20,000 $s^{-1}$ produces a local pressure of at least about 1034.2 MPa (150,000 psi) at a tip of the at least one rotor. In embodiments, the energy expenditure of the reactor is greater than 1000 watts per cubic meter of fluid therein during subjection of the reactants to the shear. The contact surface can comprise at least a portion of the at least one rotor, at least a portion of the at least one stator, or at least a portion of both. The at least one rotor can comprise at least one ring of rotor tips and/or the at least one stator can comprise at least one ring of stator tips. The rotor tips and the stator tips can be complementarily-shaped. The at least one contact surface can comprise at least a portion of the at least one ring of the rotor, at least a portion of the at least one ring of the stator, or both. In embodiments, at least a portion of the at least one stator ring is made from, coated with, or impregnated by a catalyst and at least a portion of the at least one rotor ring is made from, coated with, or impregnated by a different catalyst. The reactor can comprise at least two sets of complementarily-shaped rotor/stator rings. A contact surface of one set of rings can be made from, coated with, or impregnated by a different catalyst than a contact surface of another set of rotor/stator rings.

Subjecting the reactants to a shear rate of at least 20,000 $s^{-1}$ can comprise rotating the at least one rotor at a tip speed of at least 22.9 m/s (4,500 ft/min), wherein the tip speed is defined as πDn, where D is the diameter of the rotor and n is the frequency of revolution. In embodiments, the at least one rotor is rotated at a tip speed of at least 40.1 m/s (7,900 ft/min). In embodiments, the at least one rotor is rotated at a tip speed of at least 225 m/s (44,200 ft/min). The at least one rotor can be separated from the at least one stator by a shear gap in the range of from 1 μm (0.00004 inch) to about 4 mm (0.016 inch), wherein the shear gap is the minimum distance between the rotor and the stator. The reactor can comprise at least two generators, wherein each generator comprises a rotor and a complementarily-shaped stator. In applications, a shear rate provided by one generator is greater than a shear rate provided by another generator. In embodiments, a contact surface of a first generator is made from, coated with, or impregnated by a different catalyst than a contact surface of a second generator.

Certain embodiments of the above-described methods or systems potentially provide overall cost reduction by providing for reduced catalyst usage, permitting increased fluid throughput, permitting operation at lower temperature and/or pressure, and/or reducing capital and/or operating costs. These and other embodiments and potential advantages will be apparent in the following detailed description and drawings.

BRIEF DESCRIPTION OF THE DRAWINGS

For a more detailed description of the preferred embodiment of the present invention, reference will now be made to the accompanying drawings, wherein.

NOTATION AND NOMENCLATURE

Figure 1:
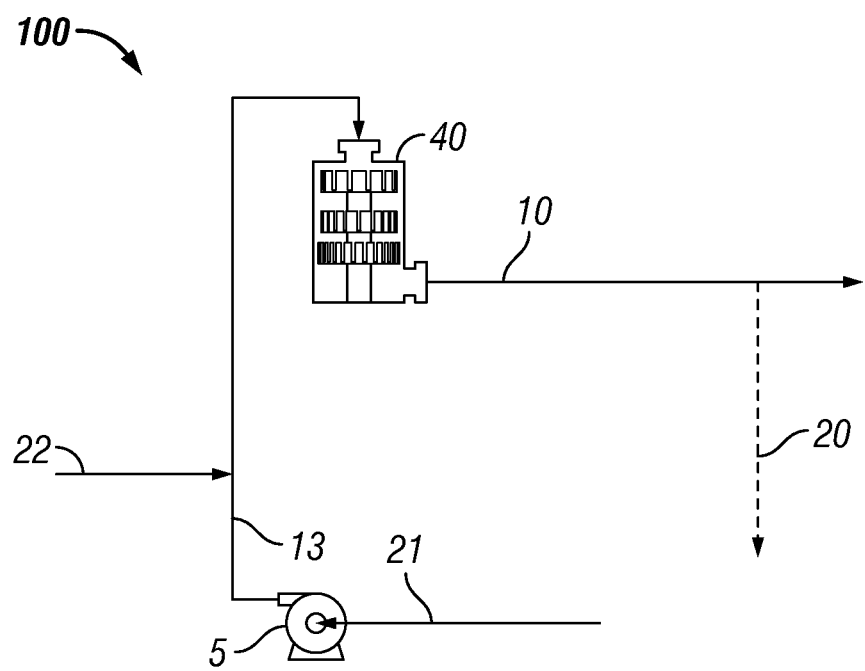
FIG. 1 is a schematic of a rotary fixed catalyst bed system according to an embodiment of the present disclosure comprising external high shear dispersing.

As used herein, the term "dispersion" refers to a liquefied mixture that contains at least two distinguishable substances (or "phases") that will not readily mix and dissolve together. As used herein, a "dispersion" comprises a "continuous" phase (or "matrix"), which holds therein discontinuous droplets, bubbles, and/or particles of the other phase or substance. The term dispersion may thus refer to foams comprising gas bubbles suspended in a liquid continuous phase, emulsions in which droplets of a first liquid are dispersed throughout a continuous phase comprising a second liquid with which the first liquid is immiscible, and continuous liquid phases throughout which solid particles are distributed. As used herein, the term "dispersion" encompasses continuous liquid phases throughout which gas bubbles are distributed, continuous liquid phases throughout which solid particles (e.g., solid catalyst) are distributed, continuous phases of a first liquid throughout which droplets of a second liquid that is substantially insoluble in the continuous phase are distributed, and liquid phases throughout which any one or a combination of solid particles, immiscible liquid droplets, and gas bubbles are distributed. Hence, a dispersion can exist as a homogeneous mixture in some cases (e.g., liquid/liquid phase), or as a heterogeneous mixture (e.g., gas/liquid, solid/liquid, or gas/solid/liquid), depending on the nature of the materials selected for combination.

The acronym "RFB" stands for "rotary fixed bed reactor." The term, "rotary fixed bed reactor" is used herein to refer to a reactor comprising at least one rotating element and containing a contact surface that is made from, coated with, or impregnated by a catalyst. The use of "fixed" in the phrase "rotary fixed bed reactor" indicates that the catalyst is "fixed" to or comprises the contact surface and is thus not free to move along the flow path (indicated by arrow 260 in FIG. 2). In instances, the catalyst is non-rotating, for example, the contact surface made from, coated with, or impregnated by catalyst may be at least a portion of a stator in a rotor/stator device. Alternatively, the fixed catalyst may rotate about the axis 260 as indicated by arrow 265 or opposite this direction, for example, the contact surface made from, coated with, or impregnated by catalyst may be at least a portion of a rotor of a rotor/stator device.

The phrase "contact surface" is used to refer to any part or portion of the RFB which comes into contact with a fluid passed through the rotary fixed bed. The contact surface may be a portion or all of a rotor, a portion or all of a stator. For example, the contact surface can be all or a portion of a circumferential ring or surface of a ring of a rotor or all or a portion of a ring or a surface of a ring of a stator.

The term, "ceramic" is used to refer to any of various hard, brittle, heat-resistant and corrosion-resistant materials formed by shaping and subsequently firing a nonmetallic mineral, such as clay, at a high temperature. Objects such as earthenware, porcelain, and tile are conventionally made of ceramic.

"Sintering" is used to refer to a method for making objects from powder, by heating the material (below its melting point) until its particles adhere to each other. The welding together and growth of contact area between two or more initially distinct particles during sintering is generally performed at temperatures below the melting point and above one-half of the absolute melting point. Sintering is traditionally used for manufacturing ceramic objects from the firing of ceramic oxides, and is also used in powder metallurgy.

The term "sintered materials" will be used herein to encompass both metallic and ceramic materials. The "sintered materials" include, but are not meant to be limited to ferrous (low and high alloy steels) and nonferrous (light and heavy) alloys, rare earth intermetallics, ceramics (oxide and nonoxide) and cermets.

The phrase "powder metallurgy" is used to refer to a metalworking process used to fabricate parts of simple or complex shape from a wide variety of metal and alloy powders. The process involves shaping of the powder and subsequent bonding of individual particles by heating and/or mechanical working. Powder metallurgy can be a highly flexible and automated process that is environmentally friendly, with low relative energy consumption and a high level of materials utilization. Powder metallurgy can be used to fabricate high-quality parts to close tolerance at low cost. Powder metallurgy processing encompasses an extensive range of ferrous and nonferrous alloy powders, ceramic powders, and mixes of metallic and ceramic powders (composite powders). Powder metallurgy processes may include pressing and sintering, powder injection molding, and full-density processing. Normally, parts made by pressing and sintering, which find many applications, require no further treatment. Such parts typically comprise pores. The properties, tolerances, and surface finish of the parts may be adjusted via secondary operations such as repressing, resintering, machining, heat treatment, a variety of surface treatments, or a combination of such secondary processes. Pore size and/or permeability can be controlled by known means, for example by incorporating leachable particles that can be dissolved after formation of the article by acid or other means.

Regardless of the processing path, part fabrication via powder metallurgy commences with a raw material in the form of a powder. A "powder" is a finely divided solid, generally smaller than about 1 mm (0.04 in.) in its maximum dimension. There are four major methods used to produce metal powders: mechanical comminution, chemical reactions, electrolytic deposition, and liquid-metal atomization. Metal powders may take a variety of shapes. Particle shape influences the surface area of the powder, its permeability and flow, and its density upon compaction. Chemical composition and purity of a powder also affect the compaction behavior of the powder.

DETAILED DESCRIPTION

Overview.

A system and process for catalytic reaction utilizing high shear contacting of reactants with a rotating structure comprising solid catalyst comprises an external high shear mechanical device to provide rapid contact and mixing of reactants in a controlled environment in the reactor/mixer device. A reactor assembly that comprises an external rotary fixed bed (RFB) or mixer as described herein may decrease mass transfer limitations and thereby allow the catalytic reaction to more closely approach kinetic limitations. Enhanced mixing may also homogenize the temperature within the reaction zone(s). Enhancing contact via the use of high shear may permit increased throughput and/or the use of a decreased amount of catalyst relative to conventional processes.

Other uses of the disclosed system and method will become apparent upon reading the disclosure and viewing the accompanying drawings. While specific examples may be presented in the following description, other embodiments are also envisioned. The embodiments described herein are exemplary only, and are not intended to be limiting. For example, the high shear rotary fixed bed system and process may be used for a variety of heterogeneously catalyzed reactions, as will become apparent upon reading the following description. Various dimensions, sizes, quantities, volumes, rates, and other numerical parameters and numbers have been used for purposes of illustration and exemplification of the principles of the invention, and are not intended to limit the invention to the numerical parameters and numbers illustrated, described or otherwise stated herein. Likewise, unless specifically stated, the order of steps is not considered critical. The different teachings of the embodiments discussed below may be employed separately or in any suitable combination to produce desired results.

System for Contacting Reactants with Heterogeneous Catalyst Via High Shear.

A high shear rotary fixed catalyst bed system will now be described in relation to FIG. 1, which is a process flow diagram of an embodiment of a high shear system 100. The basic components of a representative system include external high shear rotary fixed bed (RFB) 40 and pump 5. RFB 40 comprises at least one surface made of, coated or impregnated with a catalyst. Each of these components is further described in more detail below. Line 21 is connected to pump 5 for introducing reactants into pump 5. Line 13 connects pump 5 to RFB 40, and line 10 carries product out of RFB 40. Additional components or process steps can be incorporated between flow line 10 and RFB 40, or ahead of pump 5 or RFB 40, if desired, as will become apparent upon reading the description of the high shear process hereinbelow. For example, line 20 can be connected to line 21 or line 13 from flow line 10, such that fluid in flow line 10 may be recycled to RFB 40. Product may be removed from system 100 via flow line 10. Flow line 10 is any line into which product liquids and gases and any unreacted reactants from RFB 40 flow.

High Shear Rotary Fixed Bed.

External high shear rotary fixed bed (RFB) 40, also sometimes referred to as a rotary fixed bed or high shear rotary mixing device, is configured for receiving an inlet stream, via line 13, comprising reactants. Alternatively, RFB 40 may be configured for receiving the reactants via separate inlet lines.

Although only one RFB is shown in FIG. 1, it should be understood that some embodiments of the system can comprise two or more RFBs arranged either in series or parallel flow.

RFB 40 is a mechanical device that utilizes one or more generator comprising a rotor/stator combination, each of which has a gap between the stator and rotor. The gap between the rotor and the stator in each generator set may be fixed or may be adjustable. RFB 40 is configured in such a way that it is capable of effectively contacting the reactants with the catalyst therein at rotational velocity. The RFB comprises an enclosure or housing so that the pressure and temperature of the fluid therein may be controlled.

High shear mixing devices are generally divided into three general classes, based upon their ability to mix fluids. Mixing is the process of reducing the size of particles or inhomogeneous species within the fluid. One metric for the degree or thoroughness of mixing is the energy density per unit volume that the mixing device generates to disrupt the fluid particles. The classes are distinguished based on delivered energy densities. Three classes of industrial mixers having sufficient energy density to consistently produce mixtures or emulsions with particle sizes in the range of submicron to 50 microns include homogenization valve systems, colloid mills and high speed mixers. In the first class of high energy devices, referred to as homogenization valve systems, fluid to be processed is pumped under very high pressure through a narrow-gap valve into a lower pressure environment. The pressure gradients across the valve and the resulting turbulence and cavitation act to break-up any particles in the fluid. These valve systems are most commonly used in milk homogenization and can yield average particle sizes in the submicron to about 1 micron range.

At the opposite end of the energy density spectrum is the third class of devices referred to as low energy devices. These systems usually have paddles or fluid rotors that turn at high speed in a reservoir of fluid to be processed, which in many of the more common applications is a food product. These low energy systems are customarily used when average particle sizes of greater than 20 microns are acceptable in the processed fluid.

Between the low energy devices and homogenization valve systems, in terms of the mixing energy density delivered to the fluid, are colloid mills and other high speed rotor-stator devices, which are classified as intermediate energy devices. A typical colloid mill configuration includes a conical or disk rotor that is separated from a complementary, liquid-cooled stator by a closely-controlled rotor-stator gap, which is commonly between 0.025 mm to 10 mm (0.001-0.40 inch). Rotors are usually driven by an electric motor through a direct drive or belt mechanism. As the rotor rotates at high rates, it pumps fluid between the outer surface of the rotor and the inner surface of the stator, and shear forces generated in the gap process the fluid. Many colloid mills with proper adjustment achieve average particle sizes of 0.1 to 25 microns in the processed fluid. These capabilities render colloid mills appropriate for a variety of applications including colloid and oil/water-based emulsion processing such as that required for cosmetics, mayonnaise, or silicone/silver amalgam formation, to roofing-tar mixing.

The RFB comprises at least one revolving element that creates the mechanical force applied to the reactants therein. The RFB comprises at least one stator and at least one rotor separated by a clearance. For example, the rotors can be conical or disk shaped and can be separated from a complementarily-shaped stator. In embodiments, both the rotor and stator comprise a plurality of circumferentially-spaced rings having complementarily-shaped tips. A ring may comprise a solitary surface or tip encircling the rotor or the stator. In embodiments, both the rotor and stator comprise more than 2 circumferentially-spaced rings, more than 3 rings, or more than 4 rings. For example, in embodiments, each of three generators comprises a rotor and stator each having 3 complementary rings, whereby the material processed passes through 9 shear gaps or stages upon traversing RFB 40. Alternatively, each of three generators may comprise four rings, whereby the processed material passes through 12 shear gaps or stages upon passing through RFB 40. In some embodiments, the stator(s) are adjustable to obtain the desired shear gap between the rotor and the stator of each generator (rotor/stator set). Each generator may be driven by any suitable drive system configured for providing the desired rotation.

In some embodiments, RFB 40 comprises a single stage dispersing chamber (i.e., a single rotor/stator combination, a single high shear generator). In some embodiments, RFB 40 is a multiple stage inline disperser and comprises a plurality of generators. In certain embodiments, RFB 40 comprises at least two generators. In other embodiments, RFB 40 comprises at least 3 generators. In some embodiments, RFB 40 is a multistage mixer whereby the shear rate (which, as mentioned above, varies proportionately with tip speed and inversely with rotor/stator gap width) varies with longitudinal position along the flow pathway, as further described hereinbelow.

According to this disclosure, at least one surface within RFB 40 is made of, impregnated with, or coated with a catalyst suitable for catalyzing a desired reaction. For example, in embodiments, all or a portion of at least one rotor, at least one stator, or at least one rotor/stator set (i.e., at least one generator) is made of, coated with, or impregnated with a suitable catalyst. In some applications, it may be desirable to utilize two or more different catalysts. In such instances, a generator may comprise a rotor made of, impregnated with, or coated with a first catalyst material, and the corresponding stator of the generator may be made of, coated with, or impregnated by a second catalyst material. Alternatively one or more rings of the rotor may be made from, coated with, or impregnated with a first catalyst, and one or more rings of the rotor may be made from, coated with, or impregnated by a second catalyst. Alternatively one or more rings of the stator may be made from, coated with, or impregnated with a first catalyst, and one or more rings of the stator may be made from, coated with, or impregnated by a second catalyst. All or a portion of a contact surface of a stator, rotor, or both can be made from or coated with catalytic material.

For example, by way of non-limiting example, the disclosed apparatus and method may be used for the production of liquid product from gas comprising light gas such as methane, ethane, propane, butane, methanol, carbon dioxide, and combinations thereof. In such instances a contact surface may be made from, coated with, or impregnated with cobalt ferrite or ruthenium carbonyl to dissociate carbon dioxide and another contact surface may be made from, coated with, or impregnated with a catalyst such as silica palladium for dehydrogenating the methane. In such cases, the rotor and the stator of a generator may each comprise a different catalyst, separate rings of the stator or portions thereof may comprise different catalysts, separate rings of the rotor or portions thereof may comprise different catalysts, or one generator may comprise one catalyst and another generator another catalyst.

A contact surface of RFB 40 can be made from a porous sintered catalyst material, such as platinum. In embodiments, a contact surface is coated with a porous sintered catalytic material. In applications, a contact surface of RFB 40 is coated with or made from a sintered material and subsequently impregnated with a desired catalyst. The sintered material can be a ceramic or can be made from metal powder, such as, for example, stainless steel or pseudoboehmite. The pores of the sintered material may be in the micron or the submicron range. The pore size can be selected such that the desired flow and catalytic effect are obtained. Smaller pore size may permit improved contact between fluid comprising reactants and catalyst. By altering the pore size of the porous material (ceramic or sintered metal), the available surface area of the catalyst can be adjusted to a desired value. The sintered material may comprise, for example, from about 70% by volume to about 99% by volume of the sintered material or from about 80% by volume to about 90% by volume of the sintered material, with the balance of the volume occupied by the pores.

Although the focus of this discussion is made with respect to an RFB containing a contact surface made from, coated with, or impregnated by a catalyst, it will be apparent to those of skill in the art upon reading this description that a sintered metal catalyst-coated contact surface may be useful in non-high shear applications. By way of non-limiting examples, a reactor containing a contact surface made from, coated with, or impregnated by a catalyst may be useful in place of a conventional reactor comprising a fixed bed of catalyst, a slurry of catalyst, or a fluidized bed of catalyst.

It may be desirable to have a different porosity in each stage of RFB 40. For example, in chain lengthening homologation of hydrocarbons, the average pore size in a first generator may be less than the average pore size in a second generator, and so on along the flow path. Alternatively, the average pore size in a first stage of rings within a generator may be smaller or larger than the average pore size in a second or subsequent stage of rings (rotor/stator tips) within the generator. Alternatively, when two or more RFBs are connected in series, the average pore size of the sintered material in the first RFB may be smaller or larger than the average pore size of the sintered material in a second or subsequent RFB and so on. Utilizing a second RFB comprising a sintered material having a larger average pore size than a first RFB along the flow path may be desirable, for example, to maintain a growing chain length, and allow a liquid product to pass out of the RFB. For example, the average pore size may increase from submicron to micron to 10 micron to 100 micron or any range therebetween along the flow path; or vice versa.

Generally it is desirable that the rings defined by the tips of the rotor/stator contain no openings (i.e. teeth or grooves) such that substantially all of the reactants are forced through the pores of the sintered material, rather than being able to bypass the catalyst by passing through any openings or grooves which are generally present in conventional dispersers. In this manner, for example, a reactant will be forced through the sintered material, thus forcing contact with the catalyst.

In embodiments, the sintered material of which the contact surface is made comprises stainless steel or bronze. The sintered material (sintered metal or ceramic) may be passivated and then catalyst applied thereto. The catalyst may be applied by any means known in the art. The contact surface may then be calcined to yield the metal oxide (e.g. stainless steel). The first metal oxide (e.g., the stainless steel oxide) may be coated with a second metal and calcined again. For example, stainless steel oxide may be coated with aluminum and calcined to produce aluminum oxide. Subsequent treatment may provide another material. For example, the aluminum oxide may be coated with silicon and calcined to provide silica. Several calcining/coating steps may be utilized to provide the desired contact surface and catalyst(s). In this manner, the sintered material which either makes up the contact surface or coats the contact surface may be impregnated with a variety of catalysts. Another coating technique, for example, is metal vapor deposition or chemical vapor deposition, such as typically used for coating silicon wafers with metal.

In embodiments, a sintered metal contact surface (e.g., of the rotor or the stator) is treated with a material. For example, tetra ethyl ortho silicate (TEOS). Following vacuum evaporation, TEOS may remain in surface pores. Calcination may be used to convert the TEOS to silica. This impregnation may be repeated for all desired metal catalysts. Upon formation, coating, or impregnation, the catalyst(s) may be activated according to manufacturer's protocol. For example, catalysts may be activated by contacting with an activation gas, such as hydrogen. The base material may be silicon or aluminum which, upon calcination, is converted to alumina or silica respectively. Suitable catalysts, including without limitation, rhenium, palladium, rhodium, etc. can subsequently be impregnated into the pores.

In some embodiments, the minimum clearance (shear gap width) between the stator and the rotor is in the range of from about 0.025 mm (0.001 inch) to about 3 mm (0.125 inch). In some embodiments, the minimum clearance (shear gap width) between the stator and the rotor is in the range of from about 1 μm (0.00004 inch) to about 3 mm (0.012 inch). In some embodiments, the minimum clearance (shear gap width) between the stator and the rotor is less than about 10 μm (0.0004 inch), less than about 50 μm (0.002 inch), less than about 100 μm (0.004 inch), less than about 200 μm (0.008 inch), less than about 400 μm (0.016 inch). In certain embodiments, the minimum clearance (shear gap width) between the stator and rotor is about 1.5 mm (0.06 inch). In certain embodiments, the minimum clearance (shear gap width) between the stator and rotor is about 0.2 mm (0.008 inch). In certain configurations, the minimum clearance (shear gap) between the rotor and stator is at least 1.7 mm (0.07 inch). The shear rate produced by the RFB may vary with longitudinal position along the flow pathway. In some embodiments, the rotor is set to rotate at a speed commensurate with the diameter of the rotor and the desired tip speed. In some embodiments, the RFB has a fixed clearance (shear gap width) between the stator and rotor. Alternatively, the RFB has adjustable clearance (shear gap width). The shear gap may be in the range of from about 5 micrometers (0.0002 inch) and about 4 mm (0.016 inch).

Tip speed is the circumferential distance traveled by the tip of the rotor per unit of time. Tip speed is thus a function of the rotor diameter and the rotational frequency. Tip speed (in meters per minute, for example) may be calculated by multiplying the circumferential distance transcribed by the rotor tip, $2\pi R$, where R is the radius of the rotor (meters, for example) times the frequency of revolution (for example revolutions per minute, rpm). The frequency of revolution may be greater than 250 rpm, greater than 500 rpm, greater than 1000 rpm, greater than 5000 rpm, greater than 7500 rpm, greater than 10,000 rpm, greater than 13,000 rpm, or greater than 15,000 rpm. The rotational frequency, flow rate, and temperature may be adjusted to get a desired product profile. If channeling should occur, and some reactants pass through unreacted, the rotational frequency may be increased to minimize undesirable channeling. Alternatively or additionally, unreacted reactants may be introduced into a second or subsequent RFB 40, or a portion of the unreacted reactants may be separated from the products and recycled to RFB 40.

A colloid mill, for example, may have a tip speed in excess of 22.9 m/s (4500 ft/min) and may exceed 40 m/s (7900 ft/min), 50 m/s (9800 ft/min), 100 m/s (19,600 ft/min), 150 m/s (29,500 ft/min), 200 m/s (39,300 ft/min), or even 225 m/s (44,300 ft/min) in certain applications. For the purpose of this disclosure, the term 'high shear' refers to mechanical rotor stator devices (e.g., colloid mills or rotor-stator dispersers) that are capable of tip speeds in excess of 5.1 m/s. (1000 ft/min) and require an external mechanically driven power device to drive energy into the stream of products to be reacted. By contacting the reactants with the rotating members, which can be made from, coated with, or impregnated with stationary catalyst, significant energy is transferred to the reaction. Especially in instances where the reactants are gaseous, the energy consumption of the RFB 40 will be very low. The temperature may be adjusted to control the product profile and to extend catalyst life.

In RFB 40, a tip speed in excess of 22.9 m/s (4500 ft/min) is achievable, and may exceed 225 m/s (44,200 ft/min). In some embodiments, RFB 40 is capable of delivering at least 300 L/h at a tip speed of at least 22.9 m/s (4500 ft/min). The power consumption may be about 1.5 kW. RFB 40 combines high tip speed with a very small shear gap to produce significant shear on the material being processed. The amount of shear will be dependent on the viscosity of the fluid in RFB 40. Accordingly, a local region of elevated pressure and temperature is created at the tip of the rotor during operation of the high shear rotary fixed bed. In some cases the locally elevated pressure is about 1034.2 MPa (150,000 psi). In some cases the locally elevated temperature is about 500° C. In some cases, these local pressure and temperature elevations may persist for nano or pico seconds.

An approximation of energy input into the fluid (kW/L/min) can be estimated by measuring the motor energy (kW) and fluid output (L/min). As mentioned above, tip speed is the velocity (ft/min or m/s) associated with the end of the one or more revolving elements that is creating the mechanical force applied to the fluid. In embodiments, the energy expenditure of RFB 40 is greater than 1000 watts per cubic meter of fluid therein. In embodiments, the energy expenditure of RFB 40 is in the range of from about 3000 W/m$^3$ to about 7500 W/m$^3$.

The shear rate is the tip speed divided by the shear gap width (minimal clearance between the rotor and stator). The shear rate generated in RFB 40 may be in the greater than 20,000 s$^{-1}$. In some embodiments the shear rate is at least 40,000 s$^{-1}$. In some embodiments the shear rate is at least 100,000 s$^{-1}$. In some embodiments the shear rate is at least 500,000 s$^{-1}$. In some embodiments the shear rate is at least 1,000,000 s$^{-1}$. In some embodiments the shear rate is at least 1,600,000 s$^{-1}$. In some embodiments the shear rate is at least 3,000,000 s$^{-1}$. In some embodiments the shear rate is at least 5,000,000 s$^{-1}$. In some embodiments the shear rate is at least 7,000,000 s$^{-1}$. In some embodiments the shear rate is at least 9,000,000 s$^{-1}$. In embodiments where the rotor has a larger diameter, the shear rate may exceed about 9,000,000 s$^{-1}$. In embodiments, the shear rate generated by RFB 40 is in the range of from 20,000 s$^{-1}$ to 10,000,000 s$^{-1}$. For example, in one application the rotor tip speed is about 40 m/s (7900 ft/min) and the shear gap width is 0.0254 mm (0.001 inch), producing a shear rate of 1,600,000 s$^{-1}$. In another application the rotor tip speed is about 22.9 m/s (4500 ft/min) and the shear gap width is 0.0254 mm (0.001 inch), producing a shear rate of about 901,600 s$^{-1}$.

In some embodiments, RFB 40 comprises a colloid mill. Suitable colloidal mills are manufactured by IKA® Works, Inc. Wilmington, N.C. and APV North America, Inc. Wilmington, Mass., for example. In some instances, RFB 40 comprises the DISPAX REACTOR® of IKA® Works, Inc.

In some embodiments, each stage of the external RFB has interchangeable mixing tools, offering flexibility. For example, the DR 2000/4 DISPAX REACTOR® of IKA® Works, Inc. Wilmington, N.C. and APV North America, Inc. Wilmington, Mass., comprises a three stage dispersing module. This module may comprise up to three rotor/stator combinations (generators), with choice of fine, medium, coarse, and super-fine for each stage. This allows for variance of shear rate along the direction of flow. In some embodiments, each of the stages is operated with super-fine generator. In some embodiments, at least one of the generator sets has a rotor/stator minimum clearance (shear gap width) of greater than about 5 mm (0.2 inch). In some embodiments, at least one of the generator sets has a rotor/stator minimum clearance (shear gap width) of about 0.2 mm (0.008 inch). In alternative embodiments, at least one of the generator sets has a minimum rotor/stator clearance of greater than about 1.7 mm (0.07 inch).

Figure 2:
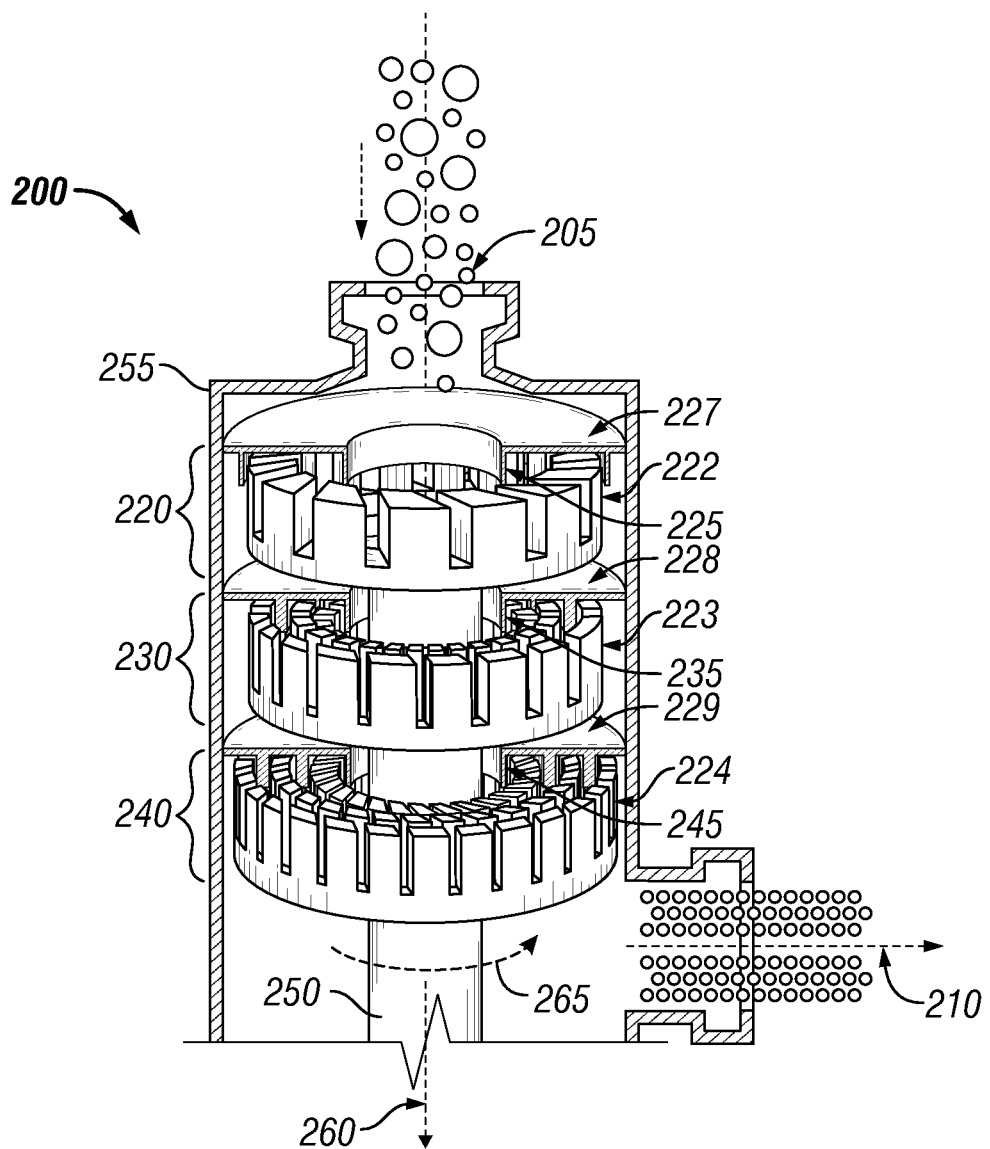
FIG. 2 is a longitudinal cross-section view of a multi-stage rotary fixed bed reactor as employed in an embodiment of the system.

In embodiments, a scaled-up version of the DISPAX REACTOR® is utilized. For example, in embodiments RFB 40 comprises a SUPER DISPAX REACTOR® DRS 2000. The RFB unit may be a DR 2000/50 unit, having a flow capacity of 125,000 liters per hour, or a DRS 2000/50 having a flow capacity of 40,000 liters/hour. Because residence time is increased in the DRS unit, the fluid therein is subjected to more shear. Referring now to FIG. 2, there is presented a longitudinal cross-section of a suitable RFB 200. RFB 200 of FIG. 2 is a dispersing device comprising three stages or rotor-stator combinations. RFB 200 is a dispersing device comprising three stages or rotor-stator combinations, 220, 230, and 240. The rotor-stator combinations may be known as generators 220, 230, 240 or stages without limitation. Three rotor/stator sets or generators 220, 230, and 240 are aligned in series along drive shaft 250.

First generator 220 comprises rotor 222 and stator 227. Second generator 230 comprises rotor 223, and stator 228. Third generator 240 comprises rotor 224 and stator 229. For each generator the rotor is rotatably driven by input 250 and rotates about axis 260 as indicated by arrow 265. The direction of rotation may be opposite that shown by arrow 265 (e.g., clockwise or counterclockwise about axis of rotation 260). Stators 227, 228, and 229 may be fixably coupled to the wall 255 of RFB 200. As mentioned hereinabove, each rotor and stator may comprise rings of complementarily-shaped tips, leading to several shear gaps within each generator.

As discussed above, a contact surface within RFB 40 is made from, coated with, or impregnated by a suitable catalyst which catalyzes the desired reaction. In embodiments, a contact surface of one ring of each rotor or stator is made from, coated with, or impregnated with a different catalyst than the contact surface of another ring of the rotor or stator. Alternatively or additionally, a contact surface of one ring of the stator may be made from coated with or impregnated by a different catalyst than the complementary ring on the rotor. The contact surface may be at least a portion of the rotor, at least a portion of the stator, or both. The contact surface may comprise, for example, at least a portion of the outer surface of a rotor, at least a portion of the inner surface of a stator, or at least a portion of both.

As mentioned hereinabove, each generator has a shear gap width which is the minimum distance between the rotor and the stator. In the embodiment of FIG. 2, first generator 220 comprises a first shear gap 225; second generator 230 comprises a second shear gap 235; and third generator 240 comprises a third shear gap 245. In embodiments, shear gaps 225, 235, 245 have widths in the range of from about 0.025 mm to about 10 mm. Alternatively, the process comprises utilization of an RFB 200 wherein the gaps 225, 235, 245 have a width in the range of from about 0.5 mm to about 2.5 mm. In certain instances the shear gap width is maintained at about 1.5 mm. Alternatively, the width of shear gaps 225, 235, 245 are different for generators 220, 230, 240. In certain instances, the width of shear gap 225 of first generator 220 is greater than the width of shear gap 235 of second generator 230, which is in turn greater than the width of shear gap 245 of third generator 240. As mentioned above, the generators of each stage may be interchangeable, offering flexibility. RFB 200 may be configured so that the shear rate will increase or decrease stepwise longitudinally along the direction of the flow 260.

Generators 220, 230, and 240 may comprise a coarse, medium, fine, and super-fine characterization, having different numbers of complementary rings or stages on the rotors and complementary stators. Although generally less desirable, rotors 222, 223, and 224 and stators 227, 228, and 229 may be toothed designs. Each generator may comprise two or more sets of complementary rotor-stator rings. In embodiments, rotors 222, 223, and 224 comprise more than 3 sets of complementary rotor/stator rings. In preferred embodiments, the rotor and the stator comprise no teeth, thus forcing the reactants to flow through the pores of the sintered material.

RFB 40 may be a large or small scale device. In embodiments, RFB 40 is used to process from less than 10 tons per hour to 50 tons per hour. In embodiments, RFB 40 processes 10 tons/h, 20 tons/h, 30 ton/hr, 40 tons/h, 50 tons/h, or more than 50 tons/h. Large scale units may produce 1000 gal/h (24 barrels/h). The inner diameter of the rotor may be any size suitable for a desired application. In embodiments, the inner diameter of the rotor is from about 12 cm (4 inch) to about 40 cm (15 inch). In embodiments, the diameter of the rotor is about 6 cm (2.4 inch). In embodiments, the outer diameter of the stator is about 15 cm (5.9 inch). In embodiments, the diameter of the stator is about 6.4 cm (2.5 inch). In some embodiments the rotors are 60 cm (2.4 inch) and the stators are 6.4 cm (2.5 inch) in diameter, providing a clearance of about 4 mm. In certain embodiments, each of three stages is operated with a super-fine generator comprising a number of sets of complementary rotor/stator rings.

RFB 200 is configured for receiving at inlet 205 a fluid mixture from line 13. The mixture comprises reactants. In embodiments, the reactants are gaseous. In embodiments, at least one reactant is gaseous and at least one reactant is liquid. Feed stream entering inlet 205 is pumped serially through generators 220, 230, and then 240, such that product is formed. Product exits RFB 200 via outlet 210 (and line 10 of FIG. 1). The rotors 222, 223, 224 of each generator rotate at high speed relative to the fixed stators 227, 228, 229, providing a high shear rate. The rotation of the rotors pumps fluid, such as the feed stream entering inlet 205, outwardly through the shear gaps (and, if present, through the spaces between the rotor teeth and the spaces between the stator teeth), creating a localized high shear condition. High shear forces exerted on fluid in shear gaps 225, 235, and 245 (and, when present, in the gaps between the rotor teeth and the stator teeth) through which fluid flows process the fluid and create product. The product may comprise a dispersion of unreacted or product gas in a continuous phase of liquid (e.g., liquid product). Product exits RFB 200 via high shear outlet 210 (and line 10 of FIG. 1).

In certain instances, RFB 200 comprises a DISPAX REACTOR® of IKA® Works, Inc. Wilmington, N.C. and APV North America, Inc. Wilmington, Mass. Several models are available having various inlet/outlet connections, horsepower, tip speeds, output rpm, and flow rate. Selection of the RFB will depend on throughput selection and desired particle, droplet or bubble size in dispersion in line 10 (FIG. 1) exiting outlet 210 of RFB 200. IKA® model DR 2000/4, for example, comprises a belt drive, 4M generator, PTFE sealing ring, inlet flange 25.4 mm (1 inch) sanitary clamp, outlet flange 19 mm (¾inch) sanitary clamp, 2 HP power, output speed of 7900 rpm, flow capacity (water) approximately 300-700 L/h (depending on generator), a tip speed of from 9.4-41 m/s (1850 ft/min to 8070 ft/min). Scale up may be performed by using a plurality of RFBs, or by utilizing larger RFBs. Scale-up using larger models is readily performed, and results from larger RFB 40 units may provide improved efficiency in some instances relative to the efficiency of lab-scale devices. The large scale unit may be a DISPAX® 2000/unit. For example, the DRS 2000/5 unit has an inlet size of 51 mm (2 inches) and an outlet of 38 mm (1.5 inches).

The product profile may be altered when using a large scale device. For example, homologation may produce longer chain hydrocarbons in large scale RFB 40 than smaller scale units, with a broader spread (wider bell curve) of product compared to small scale production (which may lead to an inverted V-type bell curve distribution of product).

Heat Transfer Devices.

Internal or external heat transfer devices for heating the fluid to be treated are also contemplated in variations of the system. For example, the reactants may be preheated via any method known to one skilled in the art. Some suitable locations for one or more such heat transfer devices are between pump 5 and RFB 40, between RFB 40 and flow line 10, and between flow line 10 and pump 5 when fluid in flow line 10 is recycled to RFB 40. RFB 40 may comprise an inner shaft which may be cooled, for example water-cooled, to partially or completely control the temperature within RFB 40. Some non-limiting examples of such heat transfer devices are shell, tube, plate, and coil heat exchangers, as are known in the art.

Pumps.

Pump 5 is configured for either continuous or semi-continuous operation, and may be any suitable pumping device that is capable of providing controlled flow through RFB 40 and system 100. In applications pump 5 provides greater than 202.65 kPa (2 atm) pressure or greater than 303.97 kPa (3 atm) pressure. Pump 5 may be a Roper Type 1 gear pump, Roper Pump Company (Commerce Georgia) Dayton Pressure Booster Pump Model 2P372E, Dayton Electric Co (Niles, Ill.) is one suitable pump. Preferably, all contact parts of the pump comprise stainless steel, for example, 316 stainless steel. In some embodiments of the system, pump 5 is capable of pressures greater than about 2026.5 kPa (20 atm). In addition to pump 5, one or more additional, high pressure pump (not shown) may be included in the system illustrated in FIG. 1. For example, a booster pump, which may be similar to pump 5, may be included between RFB 40 and flow line 10 for boosting the pressure into flow line 10.

Process for High Shear Rotary Fixed Bed Operation.

Operation of high shear rotary fixed catalyst system 100 will now be discussed with reference to FIG. 1. In operation for the production of product from reactants, reactants can be introduced into system 100 via line 21.

In embodiments, reactants or additional reactants are fed directly into RFB 40 or into line 13 via line 22, instead of being combined within line 21. Pump 5 may be operated to pump reactants through line 21, providing a controlled flow throughout high shear rotary fixed bed (RFB) 40 and high shear system 100. Pump 5 may build pressure and feed RFB 40. In some embodiments, pump 5 increases the pressure of the RFB inlet stream in line 13 to greater than 200 kPa (2 atm)

or greater than about 300 kPa (3 atmospheres). In this way, high shear system 100 may combine high shear with pressure to enhance intimate mixing of reactant(s).

The reactants are intimately mixed within RFB 40, which serves to subject the reactants to high shear. The reactants may be gaseous, liquid, or both. It is also envisaged that a catalyst may additionally be present in the reactant stream in certain embodiments. For example, a gaseous or liquid phase catalyst may be introduced to RFB 40 via inlet line 13, line 21, or line 22. Disperser IKA® model DR 2000/4, a high shear, three generator dispersing device configured with three rotors in combination with stators, aligned in series, may be used to intimately mix the reactants. The rotor/stator sets may be configured as illustrated in FIG. 2, for example. The reactant mixture may enter the RFB via line 13 and enter a first generator or rotor/stator combination. The rotors and stators of the first generator may have circumferentially spaced complementarily-shaped rings. A coarse dispersion exiting the first generator can enter a second rotor/stator combination or generator. The rotor and stator of the second generator can also comprise circumferentially spaced complementarily-shaped rings. Product and unreacted gas (if present) emerging from the second generator can enter a third rotor/stator combination, which can comprise a rotor and a stator having a number of rotor rings and stator rings, respectively. The product (which may be a dispersion if multiple phases) exits RFB 40 via line 10. In some embodiments, the shear rate increases stepwise longitudinally along the direction of the flow, 260, or going from an inner set of rings of one generator to an outer set of rings of the same generator. In other embodiments, the shear rate decreases stepwise longitudinally along the direction of the flow, 260, or going from an inner set of rings of one generator to an outer set of rings of the same generator (outward from axis 200).

For example, in some embodiments, the shear rate in the first rotor/stator stage is greater than or less than the shear rate in a subsequent stage(s). In other embodiments, the shear rate is substantially constant along the direction of the flow, with the shear rate in each stage being substantially the same.

If RFB 40 includes a PTFE seal, the seal may be cooled using any suitable technique that is known in the art. The RFB 40 may comprise a shaft in the center which may be used to control the temperature within RFB 40. For example, a water-cooled shaft may be used to moderate and extract any heat produced by exothermic reactions, such as FT conversion reactions. For endothermic reactions, heat may be added to RFB 40 (via the shaft or elsewhere, such as external to RFB 40) to promote the reaction.

The rotor(s) of RFB 40 may be set to rotate at a speed commensurate with the diameter of the rotor and the desired tip speed. As described above, the RFB (e.g., colloid mill or toothed rim disperser) has either a fixed clearance between the stator and rotor or has adjustable clearance.

In some embodiments, RFB 40 delivers at least 300 L/h at a tip speed of at least 22 m/s (4500 ft/min), and which may exceed 40 m/s (7900 ft/min), 225 m/s (45,000 ft/min) or greater. The power consumption may be about 1.5 kW or higher as desired. Although measurement of instantaneous temperature and pressure at the tip of a rotating shear unit or revolving element in RFB 40 is difficult, it is estimated that the localized temperature seen by the intimately mixed fluid is in excess of 500° C. and at pressures in excess of 500 kg/cm$^2$ under cavitation conditions. The high shear mixing may result in a product dispersion of the unreacted and product gas and/or liquid in micron or submicron-sized bubbles or droplets. In some embodiments, the resultant dispersion has an average bubble or droplet size less than or equal to about 5, 4, 3, 2, or 1 μm. In embodiments, the resultant dispersion has an average bubble or droplet size less than or equal to about 1.5 μm. Accordingly, the dispersion exiting RFB 40 via line 10 comprises micron and/or submicron-sized droplets or gas bubbles. In some embodiments, the mean bubble or droplet size is in the range of about 0.4 μm to about 1.5 μm. In some embodiments, the resultant dispersion has an average bubble or droplet size less than or about 1 μm. In some embodiments, the mean bubble or droplet size is less than or about 400 nm, and may be less than or about 100 nm in some cases. In many embodiments, the dispersion is able to remain dispersed at atmospheric pressure for at least 15 minutes.

Product exits RFB 40 via line 10, as illustrated in FIG. 1. The contents of flow line 10 may be maintained at a specified reaction temperature using heating and/or cooling capabilities (e.g., heaters) and temperature measurement instrumentation. Pressure in the flow line may be monitored using suitable pressure measurement instrumentation, employing techniques that are known to those of skill in the art.

Conditions of temperature, pressure, space velocity and reactant composition may be adjusted to produce a desired product profile. The use of RFB 40 may allow for better interaction and more uniform mixing of the reactants and may therefore permit an increase in possible throughput and/or product yield. In some embodiments, the operating conditions of system 100 comprise a temperature of at or near ambient temperature and global pressure of at or near atmospheric pressure. Because the RFB 40 provides high pressure (e.g. 150,000 psi) at the tips of the rotors, the temperature of the reaction may be reduced relative to conventional reaction systems in the absence of high shear. In embodiments, the operating temperature is less than about 70% of the conventional operating temperature, or less than about 60% of the conventional operating temperature, or less than about 50% of the conventional operating temperature for the same reaction(s)

The residence time within RFD 40 is typically low. For example, the residence time can be in the millisecond range, can be about 10, 20, 30, 40, 50, 60, 70, 80, 90 or about 100 milliseconds, can be about 100, 200, 300, 400, 500, 600, 700, 800, or about 900 milliseconds, can be in the range of seconds, or can be any range thereamong.

Multiple Pass Operation.

In the embodiment shown in FIG. 1, the system is configured for single pass operation, wherein the product produced in RFB 40 continues along flow line 10. The output of RFB 40 may be run through a sintered catalytic device. In some embodiments, it may be desirable to pass the contents of flow line 10, or a fraction thereof, through RFB 40 during a second pass. In this case, at least a portion of the contents of flow line 10 may be recycled from flow line 10 and pumped by pump 5 into line 13 and thence into RFB 40. Additional reactants may be injected via line 22 into line 13, or may be added directly into the RFB. In other embodiments, product is further treated prior to recycle of a portion thereof to RFB 40.

Multiple RFBs.

In some embodiments, two or more RFBs like RFB 40, or configured differently, are aligned in series, and are used to promote further reaction. Operation of the mixers may be in either batch or continuous mode. In some instances in which a single pass or "once through" process is desired, the use of multiple RFBs in series may also be advantageous. In embodiments, the reactants pass through multiple RFBs 40 in serial or parallel flow. For example, in embodiments, product in outlet line 10 is fed into a second RFB. When multiple RFBs 40 are operated in series, additional reactants may be injected into the inlet feedstream of each RFB. In some embodiments, multiple RFBs 40 are operated in parallel, and the outlet products therefrom are introduced into one or more flow lines 10.

Features.

The intimate contacting of reactants within RFB 40 provided by RFB 40 may result in faster and/or more complete reaction of reactants. In embodiments, use of the disclosed process comprising reactant mixing via external RFB 40 allows use of reduced quantities of catalyst than conventional configurations and methods and/or increases the product yield and/or the conversion of reactants. In embodiments, the method comprises incorporating external RFB 40 into an established process thereby reducing the amount of catalyst required to effect desired reaction and/or enabling an increase in production throughput from a process operated without RFB 40, for example, by reducing downtime involved in replacement of catalyst in a conventional slurry bed reactor. In embodiments, the disclosed method reduces operating costs and/or increases production from an existing process. Alternatively, the disclosed method may reduce capital costs for the design of new processes.

By utilizing a rotary fixed bed reactor, catalyst changeout is relatively simple compared to many conventional processes. For example, the RFB may be taken offline, and the contact surface replaced, for example, the generator replaced, in a matter of minutes. This is in contrast to, for example, slurry or fixed beds, for which catalyst replacement generally takes from several hours to months to complete. This decrease in down time provided by the disclosed apparatus and method may significantly enhance the profitability of a particular application. The apparatus may be fabricated in modular fashion, making transport and set-up convenient, even in remote locations, such as locations where "stranded gas" is found.

Without wishing to be limited to a particular theory, it is believed that the level or degree of high shear mixing may be sufficient to increase rates of mass transfer and also produce localized non-ideal conditions (in terms of thermodynamics) that enable reactions to occur that would not otherwise be expected to occur based on Gibbs free energy predictions. Localized non ideal conditions are believed to occur within the RFB resulting in increased temperatures and pressures with the most significant increase believed to be in localized pressures. The increases in pressure and temperature within the RFB are instantaneous and localized and quickly revert back to bulk or average system conditions once exiting the RFB. Without wishing to be limited by theory, in some cases, the RFB may induce cavitation of sufficient intensity to dissociate one or more of the reactants into free radicals, which may intensify a chemical reaction or allow a reaction to take place at less stringent conditions than might otherwise be required. Cavitation may also increase rates of transport processes by producing local turbulence and liquid micro-circulation (acoustic streaming). An overview of the application of cavitation phenomenon in chemical/physical processing applications is provided by Gogate et al., "Cavitation: A technology on the horizon," *Current Science* 91 (No. 1): 35-46 (2006). The rotary fixed bed of certain embodiments of the present system and methods may induce cavitation whereby one or more reactant is dissociated into free radicals, which then react. In embodiments, the extreme pressure at the tips of the rotors/stators leads to liquid phase reaction, and no cavitation is involved.

Exemplary Applications

The description has been given generally with respect to a system incorporating high shear contacting of reactants, and it is to be understood that the disclosed system and method are applicable to a plethora of reactions. Any reaction conventionally carried out using a solid catalyst in a slurry, fixed, fluid bed or other solid catalyst configuration can be carried out using the high shear rotary fixed bed reactor as described herein. For example, the disclosed RFB and method may be suitable for any heterogeneously catalyzed reaction, from catalytic reforming reactions, to hydrogenation reactions, to partial oxidation reactions, and etc. The use of a contact surface made from, coated with, or impregnated by a catalyst may be useful in non-high shear applications as well, for instance within standard fixed bed applications. For example, catalytically coated sintered metal elements may have some advantages in terms of catalyst operation and replacement, etc., relative to conventional reactors. The use of the RFB may permit successful reaction at lower temperatures, and may lead to longer catalyst life compared with non-high shear processes.

Production of Liquid Product from Light Gas:

The disclosed apparatus, system, and method may be used to produce liquid product such as higher alcohols, oxygenates, and liquid hydrocarbons from light gas, such as carbon dioxide, methane, ethane, propane, butane, methanol and ethanol. Hydrocarbons may be produced. This application may mitigate some of the theorized contributory factors of global warming.

Global warming has become a growing concern and reputable scientists believe that the main drivers are the emissions of carbon dioxide and other green house gases to the atmosphere. Methane, the major component of natural gas, is flared or released in many parts of the world, because it is found in remote locations, which make it hard to economically utilize. Burning of fossil fuels for transportation or for the production of heat and electricity is generally considered a major source of carbon dioxide emissions. Carbon dioxide is also present in many natural gas sources and typically is separated and emitted to the atmosphere. The disclosed apparatus and method may utilize remote natural gas as feedstock. In this manner, light gas such as carbon dioxide and methane can be reacted to produce alcohols and/or acetaldehyde. In the very non-ideal environment reaction environment provided by the RFB 40, alcohols and/or acetaldehyde can be created by overcoming the unfavorable thermodynamics of the reactions.

In such embodiments, light gas is converted to hydrocarbons and/or organic oxygenates. The system and method may be used to produce hydrocarbons or hydrocarbon mixtures suitable for driving conventional combustion engines or hydrocarbons suitable for further industrial processing or other commercial use. Intermediate products such as methanol or dimethyl ether may also be generated by the process disclosed herein. In an embodiment, the overall process comprises the conversion of gas selected from carbon dioxide, methane, ethane, propane, butane, pentane and combinations thereof to hydrocarbons with carbon numbers greater than 2, preferably $C_5$-$C_{10}$ hydrocarbons and/or oxygenates, such as methanol. In other instances, the method comprises the use of high shear technology for the direct conversion of methane (a major component of available natural gas) to liquid hydrocarbons, primarily organic oxygenates and other liquids. The organic oxygenate product may primarily comprise alcohols. In embodiments, the organic oxygenate product comprises methanol. In embodiments, methanol and carbon dioxide are converted into organic oxygenate product comprising ethanol.

In such applications, the catalyst of RFB reactor 40 can comprise a catalyst for dissociating carbon dioxide, such as cobalt ferrite or ruthenium carbonyl as well as nickel, rhodium and palladium containing catalyst and rare earth metal oxide catalysts. A dehydrogenation catalyst may also be present to dehydrogenate the methane or other alkane. In embodiments, the catalyst is one of the catalysts listed in Table 1.

dodecacarbonyl and MR-34-18 VII can be utilized according to this disclosure. In embodiments, the catalyst comprises palladium silica.

In embodiments, the catalyst dehydrogenates water and/or hydrocarbons such as simple alkanes thereby creating free hydrogen and hydroxyl radicals (in the case of water). The

TABLE 1

| Catalyst | Catalyst Comps. | Na/Mn | W/Mn | Ti/Mn | Si/Mn | Co/Mn | Fe/Mn | Mo/Mn | Ba/Mn | La/Mn |
|---|---|---|---|---|---|---|---|---|---|---|
| MR 34 | Na, W, Mn | 0.0667 | 0.1000 | — | — | — | — | — | — | — |
| MR 34-2 | Na, W, Mn | 0.0636 | 0.0909 | — | — | — | — | — | — | — |
| MR 34-3 | Na, W, Mn | 1.0000 | 1.0000 | — | — | — | — | — | — | — |
| MR 34-4 | Na, W, Mn | 0.2727 | 0.0909 | — | — | — | — | — | — | — |
| MR 34-5 | Na, W, Mn | 0.0412 | 0.0588 | — | — | — | — | — | — | — |
| MR 34-6 | W, Mn | — | 0.0909 | — | — | — | — | — | — | — |
| MR 34-7 | Na, W, Mn | 0.0636 | 0.0091 | — | — | — | — | — | — | — |
| MR 34-8 | Ti, Na, W, Mn | 0.0636 | 0.0909 | 0.0182 | — | — | — | — | — | — |
| MR 34-9 | Na, Mn | 0.0636 | — | — | — | — | — | — | — | — |
| MR 34-10 | Na, W, Mn | 0.0636 | 0.0545 | — | — | — | — | — | — | — |
| MR 34-11 | Si, Na, W, Mn | 0.0636 | 0.0909 | — | 0.0636 | — | — | — | — | — |
| MR 34-12 | Co, Na, W, Mn | 0.0636 | 0.0909 | — | — | 0.0636 | — | — | — | — |
| MR 34-13 | Na, W, Mn | 0.0636 | 0.1091 | — | — | — | — | — | — | — |
| MR 34-14 | Ba, Mo, Na, W, Mn | 0.0636 | 0.0909 | — | — | — | — | 0.0636 | 0.0636 | — |
| MR 34-15 | Co, Na, W, Mn | 0.0636 | 0.1091 | — | — | 0.1091 | — | — | — | — |
| MR 34-16 | Co, Na, W, Mn | 0.0600 | 0.0800 | — | — | 0.0600 | 0.0600 | — | — | — |
| MR 34-17 | Co, Na, W, Mn | 0.0636 | 0.1091 | — | — | 0.1818 | — | — | — | — |
| MR 34-18 | Co, Na, W, Mn | 0.0636 | 0.1091 | — | — | 0.2545 | — | — | — | — |
| MR-34-18 VII | Co, Na, W, Mn, La | 0.0636 | 0.1091 | — | — | 0.2545 | — | — | — | 0.008 |
| MR 34-19 | Co, Na, W, Mn | 0.0636 | 0.1091 | — | — | 0.2727 | — | — | — | — |

In embodiments, catalyst MR-34-18 or MR-34-18 VII is utilized. The catalyst can comprise at least one of iron, ruthenium, osmium, cobalt, rhodium, iridium, nickel, lanthanum, palladium and platinum or combinations thereof. In specific embodiments, the catalyst comprises ruthenium. The catalyst may comprise ruthenium carbonyl, which is also known as tri-ruthenium dodecacarbonyl [$Ru_3(CO)_{12}$]. In embodiments, a single catalyst is utilized. In embodiments, more than one catalyst is utilized. For example, both tri-ruthenium hydrogen radicals then deoxygenate carbon dioxide to form carbon monoxide that is then free to react with free hydrogen or other carbon containing radicals. As discussed hereinabove a contact surface within RFB 40 may be made from, coated with, or impregnated with a first catalyst, and a second contact surface made from, coated with, or impregnated with a second catalyst.

The product-mix in such applications may comprise methanol, ethanol, n-propanol, acetaldehyde, and/or hydrocarbons. In embodiments, the product may comprise methanol at more than 30 g/liter, ethanol at more than 15 g/liter, n-propanol at more than 2 g/liter and acetaldehyde at more than 20 g/liter, and trace amounts of hydrocarbons.

Hydrodesulfurization, Hydrodenitrogenation, Hydrofinishing.

The disclosed apparatus, system and method may be used for hydrodesulfurization, hydrodenitrogenation, and/or hydrofinishing of hydrocarbons comprising sulfur-containing compounds with hydrogen. In embodiments, at least a portion of sulfur-containing compounds in the liquid phase are reduced to form hydrogen sulfide gas. In embodiments, at least a portion of nitrogen-containing compounds in the liquid phase are converted to ammonia.

The liquid to be hydrodesulfurized, hydrofinished, or hydrodenitrogenated may comprise hydrocarbons selected from the group consisting of liquid natural gas, crude oil, crude oil fractions, gasoline, diesel, naphtha, kerosene, jet fuel, fuel oils and combinations thereof.

In such embodiments, at least one contact surface within RFB 40 is made from, coated with, or impregnated by a catalyst known to those of skill in the art to be suitable for hydrodesulfurization, hydrodenitrogenation, or hydrofinishing. A suitable soluble catalyst may be a supported metal sulfide. In embodiments, the metal sulfide is selected from molybdenum sulfide, cobalt sulfide, ruthenium sulfide, and combinations thereof. In embodiments, the catalyst comprises ruthenium sulfide. In embodiments, the catalyst comprises a binary combination of molybdenum sulfide and cobalt sulfide. In embodiments, the support comprises alumina. In embodiments, the catalyst comprises an alumina base impregnated with cobalt and/or molybdenum. The catalyst used in the hydrodesulfurization step may be a conventional desulfurization catalyst made up of a Group VI and/or a Group VIII metal on a suitable refractory support. In embodiments, the hydrotreating catalyst comprises a refractory support selected from the group consisting of silica, alumina, silica-alumina, silica-zirconia, silica-titania, titanium oxide, and zirconium oxide. The Group VI metal may be molybdenum or tungsten and the Group VIII metal usually nickel or cobalt. The hydrodesulfurization catalyst may comprise a high surface area γ-alumina carrier impregnated with mixed sulfides, typically of CoMo or NiMo. In embodiments, the hydrodesulfurization catalyst comprises $MoS_2$ together with smaller amounts of other metals, selected from the group consisting of molybdenum, cobalt, nickel, iron and combinations thereof. In embodiments, the catalyst comprises zinc oxide. In embodiments, the catalyst comprises a conventional presulfided molybdenum and nickel and/or cobalt hydrotreating catalyst.

In embodiments, the catalyst is in the aluminosilicate form. In embodiments, the catalyst is intermediate pore size zeolite, for example, zeolite having the topology of ZSM-5. Although the catalyst may be subjected to chemical change in the reaction zone due to the presence of hydrogen and sulfur therein, the catalyst may be in the form of the oxide or sulfide when first brought into contact with the carbonaceous feedstream. When the system and method are focused on hydrodenitrogenation, cobalt promoted molybdenum on alumina catalysts may be selected for hydrodesulfurization. For hydrodenitrogenation, nickel promoted molybdenum on alumina catalysts may be a desired catalyst.

Hydrocracking.

In embodiments, the RFB, system, and method are used for carrying out hydrocracking reactions involving a hydrocracking catalyst, hydrogen gas and fluid to be hydrocracked. In embodiments, the contact surface is made from, coated with, or impregnated by a catalyst that may be categorized as a dual-function catalyst which possesses both hydrocracking (acid component) and hydrogenation activity. In embodiments, the catalyst comprises at least one metal selected from noble metals such as platinum or palladium and non-noble metals such as nickel, cobalt, molybdenum, tungsten, iron, chromium and combinations of these metals. In embodiments, the catalyst comprises a combination of metals such as cobalt with molybdenum. In embodiments, hydrocracking is intended to be accompanied by some hydrorefining (desulfurization, denitrification, etc.) and the catalytic metallic component comprises nickel and molybdenum, or nickel and tungsten.

The hydrocracking catalysts may be employed with an inorganic oxide matrix component which may be selected from, for example, amorphous catalytic inorganic oxides, e.g., catalytically active silica-aluminas, clays, silicas, aluminas, magnesias, titanias, zirconias, silica-aluminas, silica-zirconias, silica-magnesias, alumina-borias, alumina-titanias and the like and mixtures thereof. Although the catalyst may be subjected to chemical change in the reaction zone due to the presence of hydrogen and sulfur therein, the catalyst may be in the form of the oxide or sulfide when first brought into contact with the dispersion of hydrogen in hydrocarbonaceous feedstream.

The acidic cracking component of the hydrocracking catalyst may be an amorphous material such as an acidic clay, alumina, silica, or amorphous silica-alumina. Longer life catalyst may comprise a high amount of molecular sieve. Such catalysts with a higher degree of molecular sieve are the "zeolite" type catalysts. In conventional usage the term "molecular sieve" refers to a material having a fixed, open-network structure, usually crystalline, that may be used to separate hydrocarbons or other mixtures by selective occlusion of one or more of the constituents, or may be used as a catalyst in a catalytic conversion process. The term "zeolite" refers to a molecular sieve containing a silicate lattice, usually in association with some aluminum, boron, gallium, iron, and/or titanium.

In embodiments, the catalyst comprises an acidic cracking component comprising a zeolite. Large pore zeolites such as zeolites X or Y may be suitable because the principal components of the feedstocks (e.g., gas oils, coker bottoms, reduced crudes, recycle oils, FCC bottoms) are higher molecular weight hydrocarbons which will not enter the internal pore structure of smaller pore zeolites and therefore will not undergo suitable conversion.

In some embodiments, the hydrocracking catalyst comprises an aluminosilicate component. Representative of the zeolitic aluminosilicates employable as component parts of hydrocracking catalysts are Zeolite Y (including steam stabilized, e.g., ultra-stable Y), Zeolite X, Zeolite beta, Zeolite ZK, Zeolite ZSM-3, faujasite, MCM-22, LZ, ZSM-5-type zeolites, e.g., ZSM-5, ZSM-11, ZSM-12, ZSM-23, ZSM-35, ZSM-38, ZSM-48, ZSM-20, crystalline silicates such as silicalite, erionite, mordenite, offretite, chabazite, FU-1-type zeolite, NU-type zeolites, LZ-210-type zeolite and mixtures thereof.

In embodiments, the catalyst comprises an amorphous material together with a crystalline zeolite, as described in U.S. Pat. No. 3,523,887. In embodiments, the catalyst is a catalyst as described in U.S. Pat. No. 5,391,287. Heavy hydrocarbon oils may be simultaneously hydrocracked and hydrodewaxed to produce a liquid product of satisfactory pour point and viscosity. This product may be obtained by the use of a catalyst comprising SSZ-35 zeolite. In embodiments, the hydrocarbonaceous feedstream in line 21 comprises heavy hydrocarbon oils [e.g., gas oil boiling above 343° C. (650° F.)] and a SSZ-35 zeolite catalyst is employed.

In embodiments, the catalyst comprises a nickel hydrogenation catalyst, for example a catalyst according to U.S. Pat. No. 3,884,798, which is a coextruded catalytic composite of an alumina-containing porous carrier material and from about 6.5 to about 10.5% by weight of a nickel component, calculated as the elemental metal. This catalyst may be employed, for example, to obtain maximum production of LPG (liquefied petroleum gas) in the propane/butane range from hydrocarbonaceous feedstock comprising naphtha, or gasoline boiling range distillates. In embodiments, a nickel catalyst is used to convert heavier feedstocks, such as kerosenes, light gas oils, heavy gas oils, full boiling range gas oils and "black oils" into lower-boiling, normally liquid products including gasolines, kerosenes, middle-distillates, lube oils, etc.

Hydrogenation of Fatty Acids.

The RFB, system and method may be used in hydrogenation of fatty acids. In such applications, a contact surface may be made from, coated with, or impregnated by a hydrogenation catalyst, and reactants comprising fatty acids and hydrogen are introduced into RFB 40 to hydrogenate the oils. Such a hydrogenation catalyst may comprise iron, ruthenium, osmium, cobalt, rhodium, iridium, nickel, palladium and platinum or a combination thereof. The unsaturated fatty acids may be chosen from myristoleic acid, palmitoleic acid, oleic acid, linoleic acid, alpha-linolenic acid, arachidonic acid, eicosapentaenoic acid, erucic acid, docosahexaenoic acid, or any combination thereof. The reactant comprising unsaturated fatty acids may be a triglyceride stream chosen from vegetable oil, rapeseed oil, animal fats, corn oil, canola oil, olive oil, cottonseed oil, safflower oil, palm oil, soya oil, sunflower oil, peanut oil, coconut oil, or any combination thereof.

Fischer-Tropsch Conversion of Synthesis Gas.

The RFB, system and method may be used for the production of liquid hydrocarbons from reactants comprising synthesis gas (carbon monoxide and hydrogen). In such embodiments, a contact surface within RFB 40 is made from, coated with, or impregnated by an FT catalyst. The Fischer-Tropsch catalyst may comprise a Group 8, 9, or 10 metal. In embodiments, the Group VIII metal is selected from iron, cobalt, ruthenium, nickel, and combinations thereof. The activity of nickel and ruthenium catalysts is conventionally not great enough for commercial use and the price of ruthenium often makes it an unattractive option. Typically, iron is much less costly, while cobalt has the advantage of higher activity and longer life. Because the use of RFB 40 may permit operation at lower temperature and more effective catalyst utilization, the disclosed system and method may make the use of ruthenium and nickel more attractive. The catalyst metal may be supported on a base material of inorganic refractory oxide, such as alumina, silica, silica-alumina, titania, zinc oxide, and Group 4 oxides. The catalyst may further comprise a promoter metal selected from ruthenium, platinum, palladium, rhenium, cerium, halfnium, zirconium, lanthanum, copper and combinations thereof.

Catalytic Conversion of Ethylene to Acetaldehyde.

The RFB, system and method may be used to produce acetaldehyde from ethylene. In such applications, at least a portion of a contact surface within RFB 40 can be made from, coated with, or impregnated by a catalyst such as palladium chloride or cupric chloride.

Production of Dialkyl Ketones.

Dialkyl ketones may be produced using the RFB, system and method of this disclosure. For example, reactant comprising ethylene and air can be catalyzed to produce diethyl ketone and isopropanol can be converted to acetone. In such applications, a contact surface can be made of, coated with, or impregnated with a suitable catalyst such as, without limitation, iron, ruthenium, osmium, cobalt, rhodium, iridium, nickel, palladium, platinum and combinations thereof.

Production of Aniline and Toluene Diamine.

Aniline or toluene diamine may be produced utilizing the RFB, system and method herein disclosed. In such applications, a contact surface is made from, coated with, or impregnated by a catalyst active for catalyzing the hydrogenation of nitrobenzene to aniline or the hydrogenation of dinitrotoluene to toluenediamine. In some embodiments, dinitrotoluene is contacted with hydrogen, in the presence of a palladium catalyst, whereby hydrogenation produces toluenediamine. In embodiments, nitrobenzene is contacted with hydrogen, in the presence of a suitable catalyst, whereby hydrogenation leads to aniline.

In some embodiments, hydrogenation catalyst comprises finely divided nickel. In some embodiments, the catalyst comprises a platinum-palladium catalyst. In some embodiments, the catalyst also includes a modifier, which in some cases comprises iron. For hydrogenation of dinitrotoluene, a palladium catalyst is used in some embodiments. The catalyst can comprise palladium or copper, optionally in combination with other metals selected from the group consisting of lead, vanadium, phosphorous, and chromium as modifiers/promoters. A group of catalysts for production of toluene diamine comprises nickel, platinum, palladium and mixtures thereof, one of which is Raney nickel.

Production of Benzoic Acid or 2-, 3-, or 4-Methyl Benzoic Acid Isomer.

Benzoic acid or methyl benzoic acid may be produced using the RFB, system, and method disclosed herein. In such instances the reactants comprise oxygen and either toluene or o-, m-, or p-xylene. In such embodiments, a contact surface within RFB 40 is made from, coated with, or impregnated by a catalyst that is active for catalyzing the partial oxidation of toluene to benzoic acid, or for catalyzing the partial oxidation of o-, m-, or p-xylene xylene to 2-, 3-, or 4-methylbenzoic acid, respectively. For example, suitable catalyst can comprise a metal oxide. The metal oxide may be cobalt oxide, for example.

Production of Cyclohexane.

Cyclohexane may be produced using the RFB, system, and method of this disclosure. In such instances, the reactants comprise benzene and hydrogen. For such applications, a contact surface is made from, coated with, or impregnated by a catalyst capable of promoting hydrogenation of benzene. Such catalysts can be selected from the group consisting of nickel, copper, palladium, platinum, chromium, manganese, iron, cobalt, zinc, molybdenum, tin, and combinations thereof. The catalyst can comprise nickel and/or copper on an aluminum or silica base. For example, a contact surface can be coated with aluminum or silicon and calcined to produce alumina or silica, respectively. Subsequent coating with a metal selected from nickel, copper, palladium, platinum, chromium, manganese, iron, cobalt, zinc, molybdenum, tin, and calcination can provide a metal oxide of the selected catalyst metal. More than one catalyst may be utilized in this manner by multiple applications of coating and calcining the contact surface.

Production of Hydrogenation Product from Aldehydes and Ketones.

The disclosed RFB, system, and method may be used for the hydrogenation of aldehydes and ketones. In such applications, the reactants comprise hydrogen gas and an aldehyde or ketone. In these applications, a contact surface of RFB 40 is made from, coated with, or impregnated by a suitable hydrogenation catalyst. Catalysts such as these generally comprise one or more transition metals or compounds of one or more transition metals in a form suitable for hydrogenation. Catalysts comprising one or more metals from group VIII or VIIIA of the periodic system of elements and/or one or more of their compounds are preferably used. The catalyst can comprise copper, zinc, iron, ruthenium, osmium, cobalt, rhodium, iridium, nickel, palladium and platinum or combinations thereof. The catalyst can comprise Raney nickel or Urushibara nickel. The catalyst metal can include chromium or other promoters; mixtures of copper and nickel and/or chromium; and a mixture of reduced copper oxide-zinc oxide. The product can comprise alcohol. In an embodiment, the catalyst is a ruthenium catalyst.

Hydration of Olefins to Produce Alcohols.

The RFB, system and method may be used in the hydration of olefins. In such embodiments, the reactants comprise an olefin and water. In such applications, a contact surface is made from, coated by, or impregnated with a suitable hydration catalyst. The catalyst can comprise, for example, oxides composed of silica, alumina, zirconia, titanium oxide, molybdenum oxide and tungsten oxide, metal phosphates such as aluminum phosphate and zirconium phosphate, and crystalline aluminosilicates called "zeolites" such as mordenite and Y type zeolite. Examples of the zeolites usable in various embodiments include crystalline aluminosilicates such as mordenite, erionite, ferrierite and ZSM zeolites developed by Mobil Oil Corp.; aluminometallosilicates containing foreign elements such as boron, iron, gallium, titanium, copper, silver, etc.; and metallosilicates substantially free of aluminum, such as gallosilicates and borosilicates. As regards the cationic species which are exchangeable in the zeolites, the proton-exchanged type (H-type) zeolites are usually used, but it is also possible to use the zeolites which have been ion-exchanged with at least one cationic species, for example, an alkaline earth element such as Mg, Ca and Sr, a rare earth element such as La and Ce, a VIII-group element such as Fe, Co, Ni, Ru, Pd and Pt, or other element such as Ti, Zr, Hf, Cr, Mo, W and Th.

Production of Ethyl Acetate.

The RFB, system, and method may be used to produce ethyl acetate. In such instances, the reactants can comprise carbonyl co-reactant and ethanol. The carbonyl co-reactant may comprise acetic acid, acetic anhydride, acetaldehyde, or a combination thereof. In these applications, a contact surface of RFB 40 is made from, coated with, or impregnated by a catalyst selected from metal catalysts comprising Pd, Ti, Ru, zeolites, or combinations thereof.

Production of Alkylene Glycol by Hydration of Alkylene Oxide.

In embodiments, the RFB, system, and method are used to form alkylene glycol by hydration of an alkylene oxide. In these applications, the reactants comprise water and alkylene oxide. The alkylene oxide gas may comprise ethylene oxide, propylene oxide, butylene oxide, or a combination thereof. The alkylene glycol may comprise ethylene glycol. For the production of alkylene glycols, a contact surface of the RFB is made from, coated with, or impregnated by a hydration catalyst. The catalyst can comprise, for example, an organometallic compound or a zeolite.

Acid catalyst may also be utilized. For example, partially amine-neutralized sulfonic acid catalysts may be used as the catalyst. These catalysts are heterogeneous and may be described more completely as sulfonic acid-type ion exchange resins. These resins are then modified by passing sufficient amine through the resin to partially neutralize the sulfonic acid groups contained therein. Primary, secondary or tertiary amines are each acceptable. Tertiary amines may be used in the disclosed process. The result is a catalyst which consists of a mixture of the original free sulfonic acid and the amine salt of the sulfonic acid, all still in the heterogeneous form. In a specific embodiment, catalyst comprises a styrene-divinylbenzene copolymer matrix with pendant sulfonic acid groups. Catalysts falling within this species are available from Rohm and Haas under the designation Amberlyst RTM 15 and Amberlyst XN-1010 which differ in the amount of surface area available. Other matrices than the styrene-divinylbenzene type could be used, including other organic polymers and inorganic materials, provided only that the substrate be capable of binding the sulfonic acid groups to maintain a heterogeneous catalyst system. Other representatives of the numerous acid catalysts that have been suggested for use in the hydration of alkylene oxides include fluorinated alkyl sulfonic acid ion exchange resins, carboxylic acids and halogen acids, strong acid cation exchange resins, aliphatic mono- and/or polycarboxylic acids, cationic exchange resins, acidic zeolites, sulfur dioxide, trihalogen acetic acids. In addition to the acid catalysts, numerous catalysts have been suggested for the hydration of alkylene oxides. For example, the catalyst may be an aluminum phosphate catalyst, organic tertiary amines such as triethylamine and pyridine, quarternary phosphonium salts, fluoroalkyl sulfonic acid resins, alkali metal halides such as chlorides, bromides and iodides of potassium, sodium and lithium, or quaternary ammonium halides such as tetramethylammonium iodide and tetraethylammonium bromide, or combinations thereof. Various metal-containing compounds, including metal oxides, may be used as catalysts for the hydrolysis of alkylene oxides. For example, a dehydrating metal oxide such as without limitation, alumina, thoria, or oxides or tungsten, titanium, vanadium, molybdenum or zirconium. Or alternatively alkali metal bases may be used such as alcoholates, oxides of titanium, tungsten and thorium. The catalyst may also comprise an organometallic compound such as vanadium, molybdenum, tungsten, titanium, chromium, zirconium, selenium, tellurium, tantalum, rhenium, uranium, and combinations thereof. More recently, U.S. Pat. No. 4,277,632, issued Jul. 7, 1981, discloses a process for the production of alkylene glycols by the hydrolysis of alkylene oxides in the presence of a catalyst of at least one member selected from the group consisting of molybdenum and tungsten.

Production of Glycerol.

The RFB, system and method may be used to produce glycerol by hydroxylation of allyl alcohol. In such instances, the reactants comprise peroxide and an olefenic alcohol. The peroxide may be provided by hydrogen peroxide, ethylbenzyl hydroperoxide, t-butyl hydroperoxide, t-amyl hydroperoxide, cumene hydroperoxide, 2-methyl-2-hydroperoxy-methyl proprionate, 2-methyl-2-hydroperoxy propanoic acid, pyrrolehydroperoxide, furan hydroperoxide, 2-butylhydroperoxide, cyclohexyl hydroperoxide, and 1-phenyl-ethylhydroperoxide, or a combination thereof. The olefinic alcohol may comprise allyl alcohol, methallyl alcohol, cinnamyl alcohol, methyl vinyl carbinol, dimethyl allyl alcohol, oleyl alcohol, methyl vinyl carbinol, crotyl alcohol, methyallyl alcohol, cyclohexenol, or combinations thereof.

Hydroxylation of the olefenic alcohol is catalyzed by a hydroxylation catalyst. In such embodiments, a contact surface of the RFB is made from, coated with, or impregnated by a hydroxylation catalyst. Suitable catalysts may be any of the catalysts normally used for hydroxylation of olefins. In embodiments, the hydroxylation catalyst is selected from a metal oxide, a tungstic catalyst, an osmium catalyst, or a combination thereof. The catalysts may comprise transition metals such as without limitation, transition metals such as zirconium, vanadium, niobium, tantalum, chromium, molybdenum, tungsten, rhenium and uranium. Examples of suitable catalysts include without limitation, a metal oxide such as tungsten oxide or molybdenum oxide, a tungstic catalyst, osmium catalysts, and combinations thereof. Further examples of suitable catalysts include without limitation, molybdenum trioxide and tungstic oxide.

Production of Polyethylene and Polypropylene.

The RFB, system and method may be used for the production of polyethylene or polypropylene. In such instances, the reactants comprise ethylene or propylene. In such instances, a contact surface of the RFB is made from, coated with, or impregnated with a suitable polymerization catalyst. The polymerization catalyst may be a Ziegler-Natta catalyst system that includes a transition metal catalyst such as $TiCl_4$ and an organo-compound of a non-transition metal of Groups IA to IIIA of the Periodic Table of the Elements, particularly organo-aluminium compounds. Ziegler-Natta catalysts are stereospecific complexes that limit incoming monomers to a specific orientation, only adding them to the polymer chain if they are oriented in a specific direction, to produce isotactic (unbranched) polymers. The transition metals may be supported on a suitable matrix material such as alumina, silica, or magnesia. Conventional Ziegler-Natta catalysts are stereospecific complexes formed from a halide of a transition metal, such as titanium, chromium or vanadium with a metal hydride and/or metal alkyl, typically an organoaluminum compound such as an alkylaluminum compound, for example, triethylaluminum (TEAL), trimethyl aluminum (TMA) or triisobutyl aluminum (TIBAL), as a co-catalyst.

In applications, metallocene based catalysts are utilized rather than Ziegler-Natta catalysts. Metallocene compounds consist of two cyclopentadienyl anions (Cp) bound to a metal center in the oxidation state II, generally corresponding to the general formula $(C_5R_5)_2M$. Other transition metal catalysts that polymerize ethylene are based on the oxides of chromium or molybdenum. Other transition metal catalyst systems include the organo-compounds of transition metals with π-allyl, cyclopentadienyl, norbornyl, benzyl, and arene groups and also compounds including groups of the type exemplified by the neopentyl and substituted silylmethyl compounds. Catalysts that promote branching of the polymer may be employed when a low-density polyethylene is sought.

While preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, and so forth). Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, and the like.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the preferred embodiments of the present invention. The disclosures of all patents, patent applications, and publications cited herein are hereby incorporated by reference, to the extent they provide exemplary, procedural or other details supplementary to those set forth herein.

What is claimed is:

1. A method for carrying out a heterogeneously-catalyzed reaction, the method comprising:
   introducing a mixture of reactants into a reactor comprising at least one contact surface made from, coated with, or impregnated by a catalyst, wherein the contact surface comprises a sintered metal or ceramic and wherein the reactor comprises at least two generators, wherein each generator comprises a rotor and a complementarily-shaped stator, and wherein at least a portion of at least one rotor of the at least two generators comprises a porous catalyst contact portion, and wherein the at least one rotor that includes the porous catalyst contact portion is configured such that substantially all of the reactants are forced through the porous catalyst contact portion during operation; and
   forming a dispersion of the reactants within the reactor by subjecting the reactants to a shear rate of at least 20,000 $s^{-1}$ in at least one of the at least two generators, wherein the dispersion comprises droplets or gas bubbles of reactant.

2. The method of claim 1 wherein the droplets or gas bubbles of reactant in the dispersion have an average diameter of less than or equal to about 5 μm.

3. The method of claim 1 wherein the reactor comprises at least two contact surfaces made from, coated with, or impregnated by catalyst.

4. The method of claim 3 wherein at least one contact surface is made from, coated with, or impregnated by a different catalyst than at least one other contact surface.

5. The method of claim 1 wherein the catalyst is selected from the group consisting of hydrogenation catalysts, hydroxylation catalysts, partial oxidation catalysts, hydrodesulfurization catalysts, hydrodenitrogenation catalysts, hydrofinishing catalysts, reforming catalysts, hydration catalysts, hydrocracking catalysts, Fischer-Tropsch catalysts, dehydrogenation catalysts, and polymerization catalysts.

6. The method of claim 1 wherein the shear rate varies along a longitudinal flowpath in the reactor.

7. The method of claim 1 wherein subjecting the reactants to a shear rate of at least 20,000 $s^{-1}$ in at least one of the at least two generators produces a local pressure of at least about 1034.2 MPa (150,000 psi) at a tip rotor of that generator.

8. The method of claim 1 wherein subjecting the reactants to a shear rate of at least 20,000 $s^{-1}$ comprises rotating the rotor at a tip speed of at least 22.9 m/s (4,500 ft/min).

9. The method of claim 1 wherein at least one rotor is separated from at least one stator by a shear gap in the range of from 1 μm (0.00004 inch) to about 4 mm (0.016 inch).

10. The method of claim 1 wherein the reactor further comprises a third generator configured with a rotor and a complementarily-shaped stator.

11. The method of claim 1 wherein a contact surface of one generator is made from, coated with, or impregnated by a different catalyst than a contact surface of another generator.

12. The method of claim 1, wherein a first shear rate provided by one generator is greater than a second shear rate provided by another generator.

13. The method of claim 1 further comprising transferring the dispersion from the reactor to a second reactor in fluid communication therewith, the second reactor comprising a contact surface comprising a sintered metal or a ceramic.

14. A method for carrying out a catalyzed reaction, the method comprising:
introducing a mixture of reactants into a reactor comprising a first generator, and a second generator, wherein each of the first and second generator comprise a rotor and a corresponding stator, and wherein each of the first and second generator comprise a contact surface made from, coated with, or impregnated by a catalyst, wherein the contact surface comprises a sintered metal or ceramic and wherein each of the rotors comprises a porous catalyst contact portion, and wherein the reactor is configured such that substantially all of the reactants are forced through the porous catalyst contact portions during passage through the reactor; and
subjecting the reactants to a shear rate of at least 20,000 s$^{-1}$, to form a dispersion comprising droplets or gas bubbles of reactant.

15. The method of claim 14, wherein the catalyst comprises platinum.

16. The method of claim 14, wherein the shear rate varies along a longitudinal flowpath in the reactor.

17. A method for carrying out a catalyzed reaction, the method comprising:
introducing a mixture of reactants into a reactor comprising a first generator, wherein the first generator comprises a rotor and a corresponding stator, wherein the rotor comprises a porous catalyst contact portion having a contact surface comprising a sintered metal or ceramic, and wherein the reactor is configured such that substantially all of the reactants are forced through the pores of the porous catalyst contact portion during passage through the reactor; and
processing the reactants in the reactor to form a dispersion comprising droplets or gas bubbles of reactant.

18. The method of claim 17 further comprising operating the reactor at a shear rate greater than 20,000 s$^{-1}$, wherein the shear rate varies along a longitudinal flowpath in the reactor.

19. The method of claim 17 wherein the reactor further comprises a second generator comprising a rotor and a corresponding stator, wherein the rotor comprises a porous catalyst contact portion, and wherein an average pore size of the pores in the porous catalyst contact portion of the rotor of the first generator is different from an average pore size of the pores in the porous catalyst contact portion of the rotor of the second generator.

20. The method of claim 1 wherein the rotor and stator of at least one of the at least two generators are ring-shaped.

* * * * *